(12) United States Patent
Nichols

(10) Patent No.: US 11,758,036 B2
(45) Date of Patent: Sep. 12, 2023

(54) SYSTEM AND APPARATUS FOR MITIGATING OF BAD POSTURE AND PROPERTY LOSS THROUGH COMPUTER-ASSISTED APPLIANCE

(71) Applicant: Andrew Nichols, Coconut Grove, FL (US)

(72) Inventor: Andrew Nichols, Coconut Grove, FL (US)

( * ) Notice: Subject to any disclaimer, the term of this patent is extended or adjusted under 35 U.S.C. 154(b) by 770 days.

(21) Appl. No.: 16/812,805

(22) Filed: Mar. 9, 2020

(65) Prior Publication Data

US 2020/0280626 A1 Sep. 3, 2020

Related U.S. Application Data

(63) Continuation of application No. 15/042,709, filed on Feb. 12, 2016, now abandoned, which is a continuation-in-part of application No. 13/549,057, filed on Jul. 13, 2012, now abandoned.

(60) Provisional application No. 61/507,255, filed on Jul. 13, 2011.

(51) Int. Cl.
| | |
|---|---|
| *G08B 13/14* | (2006.01) |
| *H04M 1/72412* | (2021.01) |
| *H04W 4/12* | (2009.01) |
| *A61B 5/00* | (2006.01) |
| *A61B 5/11* | (2006.01) |
| *H04W 4/50* | (2018.01) |
| *H04W 4/80* | (2018.01) |

(52) U.S. Cl.
CPC ....... *H04M 1/72412* (2021.01); *A61B 5/0024* (2013.01); *A61B 5/1117* (2013.01); *A61B 5/486* (2013.01); *A61B 5/7405* (2013.01); *A61B 5/746* (2013.01); *A61B 5/7455* (2013.01); *G08B 13/1427* (2013.01); *H04W 4/12* (2013.01); *H04W 4/50* (2018.02); *H04W 4/80* (2018.02); *A61B 2562/0219* (2013.01)

(58) Field of Classification Search
CPC .................. G08B 13/1427; G08B 21/0227
See application file for complete search history.

(56) References Cited

U.S. PATENT DOCUMENTS

| | | | |
|---|---|---|---|
| 5,797,089 A | 8/1998 | Nguyen | |
| 5,825,353 A | 10/1998 | Will | |
| 5,887,176 A * | 3/1999 | Griffith | G06K 19/0705 340/10.33 |
| 6,203,495 B1 | 3/2001 | Bardy | |
| 6,265,974 B1 * | 7/2001 | D'Angelo | G08B 21/0247 340/568.1 |
| 6,408,188 B1 | 6/2002 | Park | |
| 7,697,978 B1 | 4/2010 | Farazi | |
| (Continued) | | | |

*Primary Examiner* — John A Tweel, Jr.
(74) *Attorney, Agent, or Firm* — C. John Brannon; Brannon Sowers & Cracraft PC

(57) ABSTRACT

A wireless, programmable system, including one or more sensors devices, a controller device, and a wireless communication link that operationally connects the sensor device to the controller device(s). The system may alert when a sensor device and controller device exceed a predetermined threshold of distance and/or time. Controller device(s) may also be, or in addition to, a handheld computer device, such as a smartphone. In some other embodiments, the system may be used to detect body positions and/or train a user to achieve desired postures.

7 Claims, 33 Drawing Sheets

(56) References Cited

U.S. PATENT DOCUMENTS

| | | |
|---|---|---|
| 8,249,547 B1 | 8/2012 | Fellner |
| 8,717,172 B2 * | 5/2014 | Parker .................... G08B 31/00 340/568.1 |
| 8,977,228 B2 * | 3/2015 | Nichols ................. H04M 11/04 455/404.2 |
| 9,251,679 B2 * | 2/2016 | Wandel ............... E05B 73/0017 |
| 9,311,586 B2 * | 4/2016 | Robinette .......... G08B 21/0219 |
| 9,997,052 B1 * | 6/2018 | Ayers ................ G08B 21/0269 |
| 2002/0049482 A1 | 4/2002 | Fabian et al. |
| 2002/0097152 A1 * | 7/2002 | Mengrone .......... G08B 21/0227 340/539.1 |
| 2003/0046242 A1 | 3/2003 | Himmel |
| 2003/0226695 A1 | 12/2003 | Mault |
| 2006/0227047 A1 * | 10/2006 | Rosenberg ............ G01S 5/0054 342/357.55 |
| 2007/0001803 A1 * | 1/2007 | Plamoottil ............... H04B 3/36 340/2.1 |
| 2008/0214142 A1 | 9/2008 | Morin |
| 2008/0294019 A1 | 11/2008 | Tran |
| 2009/0322540 A1 | 12/2009 | Richardson et al. |
| 2010/0003958 A1 * | 1/2010 | Ray ........................ H04W 4/90 455/404.2 |
| 2010/0010387 A1 | 1/2010 | Skelton et al. |
| 2010/0010590 A1 | 1/2010 | Skelton et al. |
| 2010/0161003 A1 | 6/2010 | Malmberg et al. |

\* cited by examiner

OVERVIEW AND INSTRUCTIONS

PostureMagic™ is a biofeedback system for achieving and keeping your posture and body position goals for better health, appearance, safety and performance. Here is important information:

1. You must purchase at least one Sensor for this program. Additional Sensors may be bought at the PostureensorMagic Store. Attach Sensors to your body, garments, eyeglass frames, etc. as shown on How to Attach Sensors.

2. Power on each Sensor and add it to your network using the Sensor Manager, which also lets you set its alarm sound, range and other parameters. The Device Status & Settings page lets you view information about each Sensor.

3. The Posture & Position Settings page lets you set the posture or body position targets that you want to achieve. Once you set those targets, one or more Sensors and this device will vibrate and/or emit a distinct sound to let you know you have either achieved your goal, or have deviated from it.

4. The Biofeedback Alerts page is automatically activated each time a Sensor alarm goes off. It illustrates for you the movement of one or more specified body parts that have triggered the alarm.

5. The Progress Chart page lets you check your progress over time in reaching posture and body position goals.

---

MAIN MENU

---

Terms of Use    Help

©All Rights Reserved 2011.    English (US)

Fig. 4B

DEVICE STATUS & SETTINGS

| Sensor # | Status | Body Part | Sensor Alarm Sound |
|---|---|---|---|
| 1 | On | Right Shoulder | On – Bell |
| 2 | On | Left Shoulder | On – Chime |
| 3 | Off | Center Upper Back | Off - Gong |
| 4 | On | Base of Spine | On -.Harp |
| 5 | Off | Rear Right Calf | Off – Low Pitch Ring |
| 6 | On | Rear Left Calf | Off – Piano Riff |
| 7 | On | Head | Off – Fog Horn |

To add Sensors or modify settings, go to <u>Sensor Manager</u>

---

This computer or smart-phone device:

| Vibration Alarm | Inactive |
|---|---|
| Sound Alarm | Active |
| Visual Alarm | Active |

To modify settings, go to <u>Sensor Manager</u>

---

<u>MAIN MENU</u>

Fig. 5A

SENSOR MANAGER — 604

You must configure each Sensor. Since more than one user may use the program, the Sensor information and data collected from Sensors can be set for each user.

Enter User information: First Name: _____ Last Name:_____

To program a Sensor for the first time or to modify its settings, turn it on, move it close to this device, and Click here ▪. The Sensor will beep 3 times to let you know you can now begin programming.

Click here to assign a number to this Sensor ▪

Click here to select this Sensor's alarm sound ▪

Click here to associate the Sensor with a part of your body ▪

Click on either:
     ▪ Deviation-based alarm: use this setting to train yourself to avoid certain postures and positions. For example, if you want to hold you head upright when you are at the computer, by selecting this option, an alarm will go off if your head leans forward.
     ▪ Achievement-based alarm: use this setting to train yourself to attain posture and position goals. For example, if you use this Sensor to train yourself to keep your feet shoulder length apart when skiing, the alarm will go off once you meet, and for as long as you maintain, that stance.

Tolerance settings: Before an alarm will go off, this Sensor has been pre-programmed to require a deviation of more than 5% from the target that continues for at least 3 seconds. Click here to change the default settings: ▪

Turn Sensor on or off: ▪ On   ▪ Off

▪ Click here if you want this device to vibrate whenever an alarm is triggered in the Sensor ▪ Click here if you want this device to play a sound whenever an alarm is triggered in the Sensor (if so, the sound in this device will be the same as the sound programmed for the Sensor).

▪ Click here to save all changes for this Sensor.

MAIN MENU

Fig. 5B

POSTURE & POSITION SETTINGS
Use this page to set your posture or body position targeted.

Select user: ■

Please click on one of the following images to select the activity you want to monitor for posture/body position feedback:

More: ⟶

Click here ■ to select the Sensor(s) you will use for this activity. Put the Sensor(s) on your body generally in the areas shown below (see How to Attach Sensors). Make sure the Sensor(s) are turned on.

While viewing the Body Image Field below, slowly move your body until you are in your targeted position. Once you are in that position, click here to save the target: ■

Body Image Field

The blue line for each Sensor is your target, and the dark gray, dashed lines represent permitted deviations from the target. Once your body position deviates beyond the permitted range for the permitted time period, alarms will be triggered in the Sensor(s) and this device. You can change deviation and time settings from the Sensor Manager.

Sensor # 1 – Head
Permitted Deviations:
Degree = 10%
Time = 5 Seconds

Sensor # 2 – Rt Shoulder
Permitted Deviations
Degree = 15%
Time = 8 Seconds

Sensor # 2 – Lt Shoulder
Permitted Deviations
Degree = 15%
Time = 8 Seconds

■ Click here to begin this biofeedback training session.

MAIN MENU

Fig. 6

HOW TO ATTACH SENSORS

There are many ways of attaching Sensors to your body or apparel. Each Sensor kit includes self-adhesive backs that allow you to affix Sensors directly to your skin or clothes. You can also go to the Sensor Store to order specialized attachment devices.

Click on an area of the body below, and you will see different attachment options available to you.

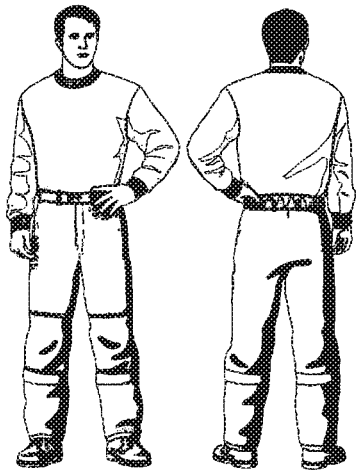

Click on the images below for more suggestions on ways you can secure Sensors to your body, accessories and clothes.

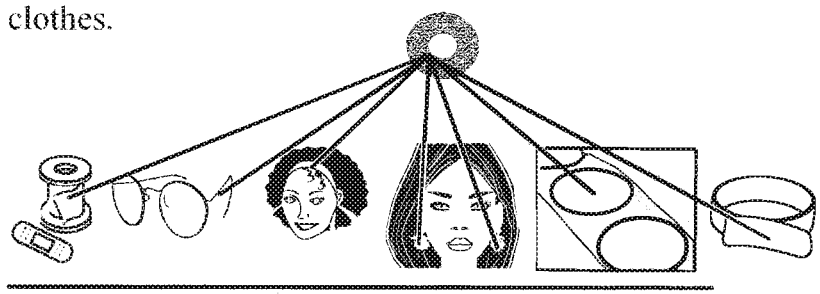

MAIN MENU

SYSTEM OVERVIEW AND INSTRUCTIONS

The TwinGuard\U+2122 Software Program lets you easily create an automated, personal security system on the go, at home, or anyplace else. Here is some important information:

1. You must purchase a Controller device and at least one receiver (Twin) device. Additional Controllers and Twins may be added at any time (TwinGuard Store).
2. Install the TwinGuard™ Software Program on your Computer Device to set up your personal security system.
3. Once you have installed the program, power on the Controller and each Twin and add them to your computer network using Device Settings.
4. The Protected List page lets you associate each Twin with the person, pet or object you wish to protect.
5. If a device moves out of range (i.e., it is taken or left behind), an alarm will go off in the device, Controller, and your Computer Device for the Alarm Cycle. After that period, alarms will cease until the lost device is brought back within range (and the device is "found"). Once found, alarms will again go off in all devices.
6. The Device Settings page lets you add devices to your computer Network; set the alarm sound each device makes when it is lost or found; and set the range for each device (i.e., how far away from the Controller a Twin must be moved before an alarm goes off).
7. Use the Emergency Notifications page to have phone, text or email notices automatically sent to recipients and you when a security breach occurs.
8. Turn the Controller and Twins on and off manually using the I/O switch, or remotely using Device Settings.
9. If you have lost an item with a Twin, find it with the Find & Seek function. Your Computer Device can send a Find Signal to search for a missing Controller or Twin Device. It will sound an alarm when a Twin device is within range of the Controller device.
10. If you have purchased the Deluxe Controller, it has a Panic Button allowing you to initiate automatic dialing for 911, EMS or other emergency services. Got to Personal 911 Assistance.

MAIN MENU

© All Rights Reserved 2011.   English (US)   Terms of Use   Help

Fig. 16B   802

TwinGuard™ Personal Security System
Protected List

Active Security Network Devices

| Device | Status | Distance/Range | Sound | Protects |
|---|---|---|---|---|
| 1 | On | 1 Ft | Air Raid | Wallet |
| 2 | On | 3 Ft | Gong | Purse |
| 3 | Off | 300 Ft | Chirp | Fido |
| 4 | On | 50 Ft | Whistle | Laptop |
| 5 | Off | 500 Ft | Bells | Junior |
| 6 | On | 20 Ft | Whistle | Cellphone |
| 7 | Off | 100 Ft | Foghorn | Car Keys |
| Controller | On | Panic Button (1 click) | Silent | User |
| Controller | On | Panic Button (Continuous Click) | Police Siren | User |
| Controller | On | Panic Button (2 or 3 clicks) | Police Siren | User |

To add devices or modify settings, go to Device Settings

Optional Alert Messages
(In Event of Security Breach Notify)

| Device | Contact | Method |
|---|---|---|
| 1 | None | Alarm Only |
| 2 | User | Text |
| 3 | User, Jane | Phone/Text |
| 4 | User | Text |
| 5 | User, Mom, Police | Phone, Text, Email |
| 6 | User, Office | Phone/Email |
| 7 | User | Phone, Text |
| 8 | User, Jane, Office, Police | Phone, Text, Email |

To add contacts or modify settings, go to Emergency Notifications

MAIN MENU

Fig. 16C

TwinGuard™
Personal Security System

Emegency Notifications

With TWINGUARD™ installed on your Computer Device, Emergency Notification Alerts can automatically be sent to you and up to other 2 recipients as long as your Computer Device is on and connected to the TWINGUARD™ network. An Alert may be programmed for each Twin Device, which may include your Computer Device. Once programmed, if a Lost Alarm continues past the Alarm Cycle, an Alert will be sent. Alerts are pre-recorded messages that may be voice, text and/or email (depending on your computer's features). Follow the directions below to set up Alerts

Select Twin Device Number for each device you wish to program to trigger an Alert by using the drop-down menu: ? [1_]

Enter User Information: First Name: _____ Last Name:_____Voice Phone #: (___)___-___; Text Message #: (___)___-___; Email Address:_____@___ to be used for Alerts.

Select Recipients: Use the drop-down menu to add recipients you want to receive Alerts: ▽[User]

Message to be delivered - Each recipient will receive the following Alert, and the bold sections will automatically be filled in by your Computer Device. You can add up to 20 words to the end of this message by clicking here:☐

[Please be advised that [User Name] has had a [wallet] removed from a TWINGUARD™ security network at __:__ o'clock [AM][PM] on __/__/20__]

Click here to accept Notification settings for this Device

To add devices or modify settings, go to Device Settings

MAIN MENU

Fig. 16E

**TwinGuard™
Personal Security System**

---

911 Assistance

---

If you have a Deluxe Controller, it has a Panic Button that if pushed, causes messages to automatically be sent to 911 for police, EMS, or fire assistance. The network can also automatically alert up to 2 recipients (in addition to 911) that an emergency is in progress. Those recipients will receive duplicates of each 911message.

Generally, your location will be determined by 911 operators using their own positioning equipment. If your call is being originated from a Network Phone, the message to 911 will include the Fixed Location for that phone. Certain TwinGuard™ systems will send GPS Coordinates from your Handheld Device.

Click here ☐ to set up user and recipient information.

There are 3 types of automated calls generated based on the number of times you press the Panic Button:

1 Click = you are in imminent danger of assault/bodily harm. An automated 911 Message requesting police assistance will be sent from your Handheld Device or Network Phone to 911 by phone. You may program your device to use Silent Dialing (if available), or Speakerphone mode.

2 Clicks = a medical/health emergency has occurred; you are incapacitated and unable to use a phone, and need immediate assistance. An automated EMS Message requesting EMS assistance will be sent from your Handheld Device or a Network Phone to 911 by phone in Speakerphone mode if available.

3 Clicks = fire danger where you are unable to use a phone, and need fire rescue. An automated EMS Message requesting fire rescue assistance will be sent from your Handheld Device or a Network Phone to 911 by phone in Speakerphone mode if available.12

---

Holding your Panic Button for more than 5 seconds will sound a siren alarm in the Controller and this device. It will ring continuously for 5 minutes unless discontinued by 4 clicks of the Panic Button.

---

Pushing your Panic Button 4 times within 30 seconds after first clicking on the Panic Button will cancel a 911 call.

---

\* Features of this program, including Silent Dialing, Speakerphone mode and GPS Coordinates will vary depending on the functionality of the Handheld Device and/or Network Phone you are using. Communications between the Controller and Handheld Device and/or Network Phone, and message delivery by the Handheld Device and/or Network Phone will only work if all devices are turned on.

---

MAIN MENU

Fig. 16F

**TwinGuard™
Personal Security System**

**Definitions Relating To
Personal 991 Assistance Functions**

911 Message is the following pre-recorded message that will automatically be sent to 911 by voice and/or text message* if the Panic Button is pressed once: "My name is [User Name] and I am in immediate peril. This message is being sent to you by an automated alarm service because I cannot use my phone without risking bodily harm. Please send help immediately. My phone number is [User Cell or Landline #], but do not call me back on this number. Doing so may jeopardize my safety. If you require confirmation, please call [Contact Person] at [Contact Person's phone number]."

EMS Message is the following pre-recorded message that will automatically be sent to 911 by voice and text message* if the Panic Button is pressed twice: "My name is [User Name] and my phone number is [User Cell or Landline #]. I need immediate medical assistance, and cannot use my phone, so this message is being sent by an automated alarm service. If you require confirmation, please call [Contact Person] at [Contact Person's phone number]." If applicable, the following message will be appended to an EMS Message: "Please be advised that I have the following medical conditions which may require special attention: [Inputted from User set-up page].

Fire Message is the following pre-recorded message that will automatically be sent to 911 by voice and text message* if the Panic Button is pressed three times: "My name is [User Name], my phone number is [User Cell or Landline #], and I am in immediate fire danger. This message is being sent to you by an automated alarm service because I cannot use my phone. Please send fire rescue as quickly as possible. If you require confirmation, please call [Contact Person] at [Contact Person's phone number]."

* Subject to availability of 911 text message services in the applicable area.

** If a call originates from a user's home or other fixed location through a Computer Phone, the User's address will automatically be appended to the message

MAIN MENU

Fig. 16G

SYSTEM AND APPARATUS FOR MITIGATING OF BAD POSTURE AND PROPERTY LOSS THROUGH COMPUTER-ASSISTED APPLIANCE

CROSS-REFERENCE TO RELATED APPLICATIONS

This patent application is a continuation application of, and claims priority to, co-pending Ser. No. 15/042,709, filed on Feb. 12, 2016, which was a continuation-in-part of U.S. patent application Ser. No. 13/549,057, filed Jul. 13, 2012, now abandoned, which claimed priority to U.S. Provisional Patent Application Ser. No. 61/507,255, filed on Jul. 13, 2011. The disclosures of these foregoing applications are incorporated herein by reference in their entirety.

TECHNICAL FIELD

The novel technology relates generally to the field of electronic devices, and, more specifically, to electronic personal and property security devices.

BACKGROUND

Many activities performed on a frequent basis, such as riding in a vehicle or locating items, present repeated and unnecessary hindrances to everyday lives. A great deal of time and energy is spent looking for car keys or a smartphone, and habituation of bad habits, such as bad posture, further affect health and wellness.

Miniaturization of technologies presents a potential boon to resolving these hindrances. However, most technologies aimed at resolving such everyday hindrances require excessively sized solutions and/or complicated configuration routines. Ultimately, what is needed is a compact, simple solution for location and awareness in one's life.

The present novel technology addresses these needs.

SUMMARY

The present novel technology relates to object location and special awareness systems.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIG. 4B depicts screenshots for portions of the System of FIG. 1, more specifically an Overview and Instructions page.

FIG. 5A depicts screenshots for portions of the System of FIG. 1, more specifically a Device Status and Settings page.

FIG. 5B depicts screenshots for portions of the System of FIG. 1, more specifically a Sensor Manager page.

FIG. 6 depicts screenshots for portions of the System of FIG. 1, more specifically a Posture and Position Settings page.

FIG. 7B depicts sample screenshots for portions of the System of FIG. 1, more specifically a How to Attach Sensors page.

FIG. 16B illustrates screenshot of the System of FIG. 9, more specifically a System Overview and Instructions page.

FIG. 16C illustrates screenshot of the System of FIG. 9, more specifically a Protected List page.

FIG. 16E illustrates screenshot of the System of FIG. 9, more specifically an Emergency Notifications page.

FIG. 16F illustrates screenshot of the System of FIG. 9, more specifically a "911" Assistance page.

FIG. 16G illustrates screenshot of the System of FIG. 9, more specifically a first Definitions page.

DETAILED DESCRIPTION

Figure 1:
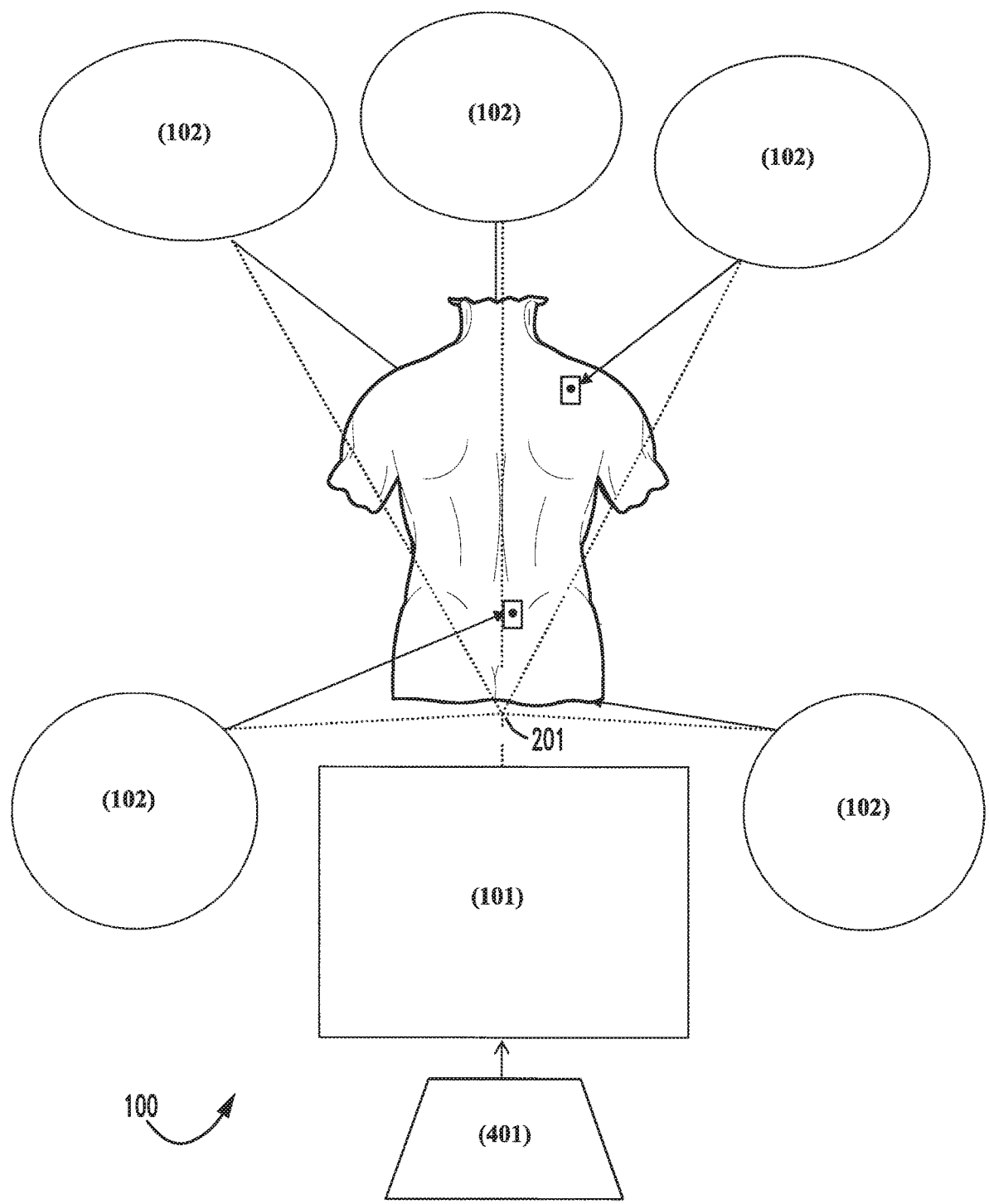
FIG. 1 depicts a schematic diagram of a System of a first embodiment of the present novel technology.

For the purposes of promoting an understanding of the principles of the novel technology and presenting its currently understood best mode of operation, reference will now be made to the embodiments illustrated in the drawings and specific language will be used to describe the same. It will nevertheless be understood that no limitation of the scope of the novel technology is thereby intended, with such alterations and further modifications in the illustrated devices and such further applications of the principles of the novel technology as illustrated therein being contemplated as would normally occur to one skilled in the art to which the novel technology relates. Some embodiments may omit some of the components of system 100, and some embodiments may include other components as well. The illustrated embodiments in the drawings are intended to be exemplary only.

FIG. 1 depicts the present novel technology as a system 100 and its component devices and representative parts of the body monitored for positional changes. System 100 includes one and/or more sensor devices 102 programmed to detect changes in posture and/or body position through an internal gyroscope and/or based on wireless measurement of the distance between another sensor 102. Each sensor may typically include a built-in vibration, visual, and/or sound device activated by changes in body position. Such changes are also wirelessly communicated to a remote controller 101 that also has built-in sound and/or vibration devices. Controller 101 may be a specially-made transceiver device, and/or a conventional, programmable device on which system software 401 may be installed (e.g., smartphone, handheld computer, PDA, PC, etc.). Controller 101 maintains a communication link 201 with each sensor, typically via BLUETOOTH (BLUETOOTH is a registered trademark of SIG, Inc., a Delaware corporation, located at 5209 Lake Washington Boulevard, Suite 350, Kirkland, Wash. 98033), infrared, radio frequency, and/or other technologies. Sensors 102 are attached to and/or worn on a person's body (or on clothing and/or accessories) through adhesion, straps, hair and/or other clips, bindings and/or other mechanisms 114. For certain embodiments of system 100, system software 401 may be installed on controller 101, which may display on an internal screen and/or external monitor real-time body position information based on communication from one and/or more sensors. In some implementations, as will be described elsewhere in this application, controller 101 may be a specially made device and/or a conventional computing device (e.g., a smartphone, PDA, laptop, desktop, etc.), which may in turn be programmed with system software 401.

In operation, system 100 may be designed to provide a user with almost immediate feedback about changes in body position and/or posture. Such biofeedback may be used to teach and/or train a user to avoid undesirable, and/or achieve desired, body positions and/or postures. To do so, each sensor 102, typically having the form of a fob-like object, may be actuated automatically to notify the user by an alarm (vibration and/or sound) once either and/or both (i) it deviates from and/or achieves, preset, horizontal and/or vertical planes; and/or (ii) it comes within a preset range of, and/or moves more than a preset distance from, another sensor. Once an alarm is actuated in a sensor, a similar vibration and/or sound alarm may also be wirelessly activated in controller 101, and/or the sound in controller 101 may be programmed to be identical to that of the specific sensor that triggers the initial alarm. By being attached to and/or worn, directly and/or indirectly (e.g., skin, shirt, headband, hairclip, eyeglass frame, etc.), on specific parts of the body, once an alarm is activated in a sensor, the user typically may be able to feel the vibration on and/or about the body part. Sensors 102 may have individualized digital signatures recognized by controller 101 through wireless communication system 201 so as to distinguish it from other sensors that may be part of system 100.

The controller 101 remotely controls the settings for each sensor 102 through wireless communication system 201. Settings may include horizontal and/or vertical planes; sound and/or vibration alarms; distances and/or ranges between sensors; and/or associations of each sensor with a body part. An alarm (audible and/or vibratory) may be set off in controller 101 and/or sensor if either of both (x) a body part to which a sensor is affixed deviates from, and/or achieves, preset horizontal and/or vertical planes; and/or (y) two and/or more paired sensors move beyond, and/or come within, preset ranges and/or distances of each other.

The sensors 102 typically may be small (e.g., the size of a quarter and/or half dollar coin), battery powered programmable transceivers. They may be attached to and/or worn on a user's body and/or clothes through various means, including adhesive backing, straps, hair and/or other clips, and/or bands. Each sensor 102 may be programmed with a distinct alarm sound and/or volume. Devices in system 100 typically may communicate with each other using BLUETOOTH, WI-FI, direct-to-device (D2D) communication protocols (e.g., WI-FI DIRECT (WI-FI DIRECT is a registered trademark of Wi-Fi Alliance, a California corporation, located at 10900-B Stonelake Boulevard, Suite 126, Austin, Tex. 78759); Long Term Evolution (LTE) D2D (LTE is a registered trademark of Institut Européen des Normes; a French nonprofit telecommunication association, located at 650 route des Lucioles, F-06921, Sophia Antipolis, France), LTE Advanced (LTE-A) D2D, etc.), radio wave, and/or other technologies 201.

Figure 2A:
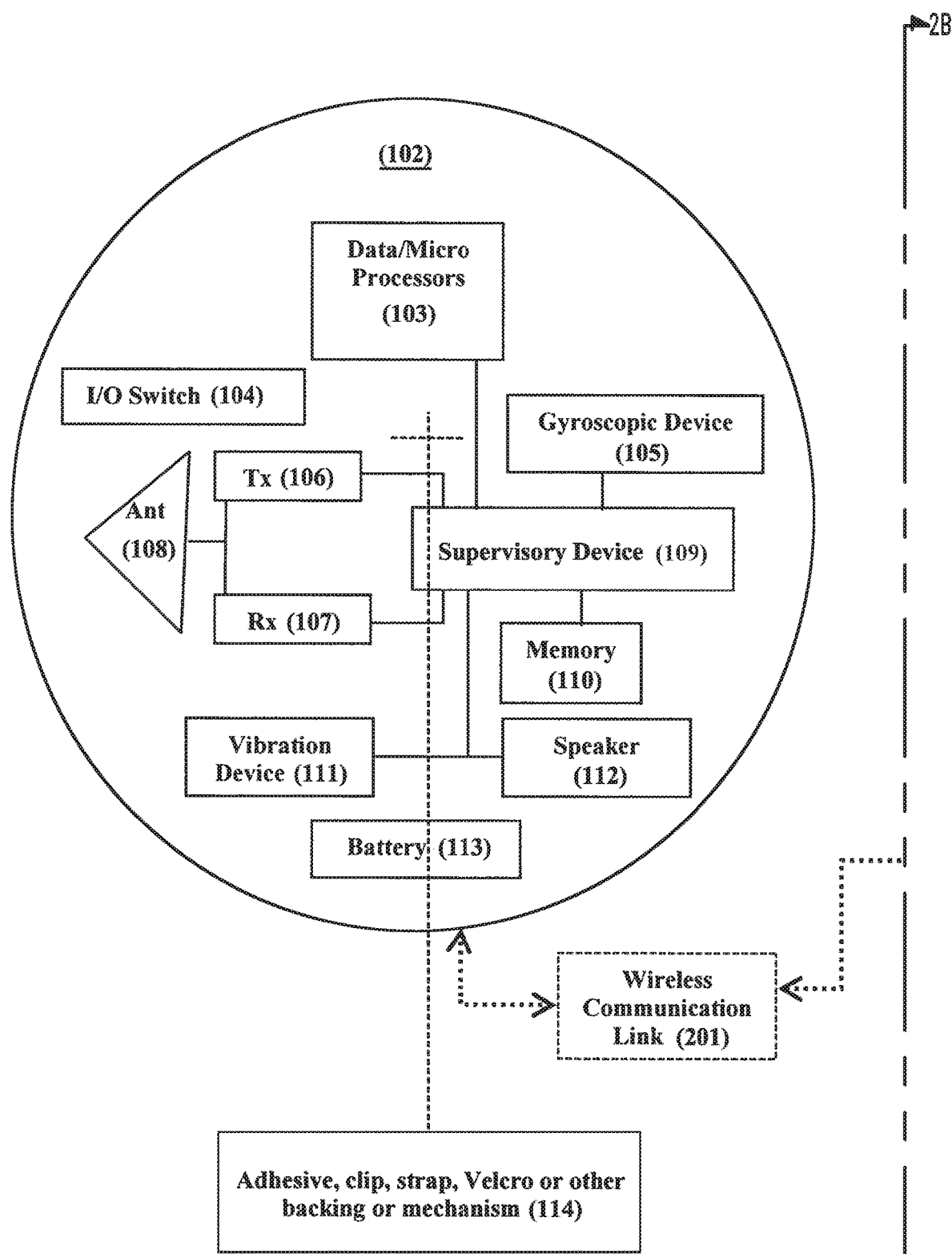
FIG. 2A depicts a schematic representation of a subset of System in the embodiment of FIG. 1.

FIG. 2A illustrates certain internal components of the devices included in system 100, which are intended to be exemplary only. As shown in FIG. 2A, each sensor 102 includes a housing containing circuitry and/or other components that may include the following:

(i) A data processor and/or microprocessor 103.
(ii) An on-off switch 104.
(iii) An orientation device 105 (e.g., gyroscope, accelerometer, etc.) for detecting and/or communicating pitch, roll, and/or yaw of sensor 102;
(iv) Circuitry for external data communication with controller device 101 and/or in certain embodiments other sensors 102, including a transmitter 106, receiver 107, and/or an antenna 108 that transforms electromagnetic energy to electrical signals provided to receiver 107, and/or transforms electrical signals from transmitter 106 to electromagnetic energy for transmission to remote radio receivers in controller 101 and/or other sensors 102. Receiver 107 responds to the electrical signals from antenna 108 to produce detected data for supervisor device 109. Receiver 107 may include circuits such as filters and/or demodulators. Transmitter 106 responds to formatted data from supervisor device 109 to provide the electrical signals to drive antenna 108. Transmitter 106 may include circuits such as modulators and/or filters. Antenna 108, receiver 107 and/or transmitter 106 together form a radio communication circuit for two-way radio and/or other wireless communication with remote radio devices such as controller 101 and/or other sensors 102.
(v) One or more supervisor devices 109 to control the operation of each sensor 102, which may be implemented as a processor, microprocessor, digital signal processor (DSP), and/or any other logic circuit and/or combination of circuits providing control functions; and/or may operate in response to data and/or to program instructions stored in memory 110; and/or may also control radio and/or other wireless communication circuit components (e.g., 106, 107, 108) by directing the tuning, activation, and/or deactivation of the circuit.
(vi) A memory unit and/or device 110 capable of storing data.
(vii) A vibration device 111 that causes sensor 102 to vibrate.
(viii) A speaker and/or other sound system 112 capable of emitting a variety of sounds (e.g., siren, beep, whistle, gong, etc.).
(ix) A power source 113 (e.g., battery, power supply, capacitor, etc.) and/or conductors 113 to operate sensor 102.
(x) Attachment mechanisms and/or devices 114 by which sensor 102 may be affixed to and/or worn on and/or about a person's body. Such systems and/or devices may include adhesives, hook-and-loop fasteners, like backings, and/or clips.

Figure 2B:
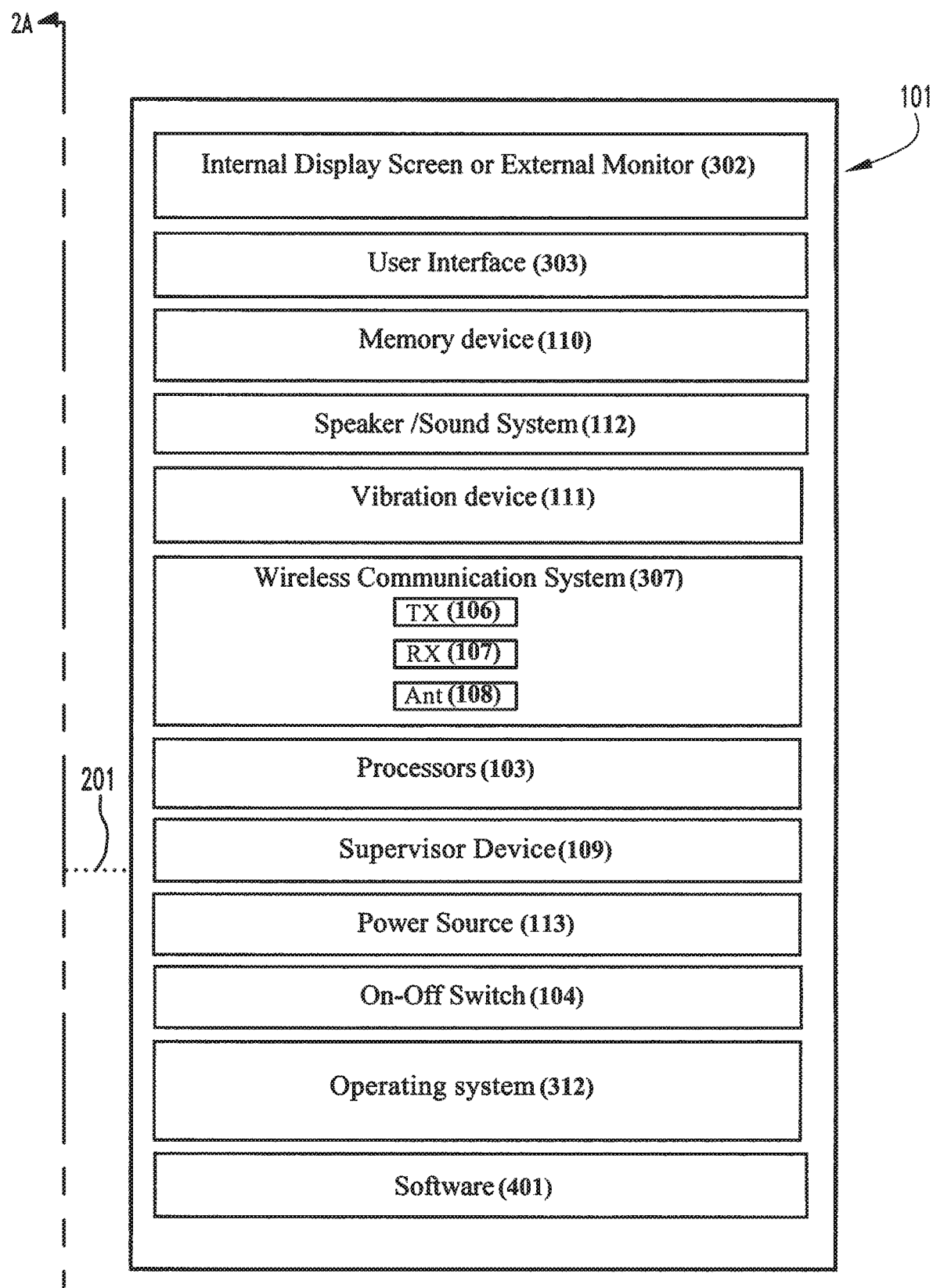
FIG. 2B depicts a second schematic representation of a subset of System in the embodiment of FIG. 1.

Also as shown in FIG. 2B, controller 101 may be a device wirelessly linked to and/or and or controlling of the settings/communications of sensor 102. Controller 101 may be a specially-made transceiver device and/or a conventional device (e.g., smartphone, PDA and/or computer) on which software programs 401 may be installed, in either case that may include a housing, circuitry, and/or other components that may include all and/or some of the following:

(i) An internal display screen and/or external monitor 302 enabling a user to view menu options, obtain information about and/or program sensors 102.
(ii) User Interface 303 comprised of a keyboard, keypad, touchscreen, etc. to let user enter data and/or perform programming functions. In some implementations, screen 302 may be user interface 303 (e.g., as a touchscreen).
(iii) A memory unit and/or device 110 capable of storing data.
(iv) A speaker and/or other sound system 112 capable of emitting a variety of sounds (e.g., siren, beep, whistle, gong, etc.).
(v) A vibration device 111 that causes controller 101 to vibrate.
(vi) A wireless communication system 307 (e.g., transmitter 106, receiver 107, and/or antenna 108) for BLUETOOTH, radio wave and/or other communications with each sensor 102.
(vii) A data processor and/or microprocessor 103.
(viii) A supervisor device 109 that may be implemented as a processor, microprocessor, digital signal processor (DSP), and/or any other logic circuit and/or combination of circuits providing control functions. It may operate in response to data and/or to program instructions stored in memory 110, and/or may control radio and/or other wireless communication circuit 307 by directing the tuning, activation, and/or deactivation of the circuit.
(ix) A power source (e.g., battery, line power, capacitors, etc.) and/or conductors 113.
(x) An on-off switch 104.
(xi) Programs and/or operating systems 312 to enable system software and/or application 401 to be installed and/or run on controller 101, which software and/or application may be configured as computer readable program code and/or stored in device's memory 110.

Figure 3B:
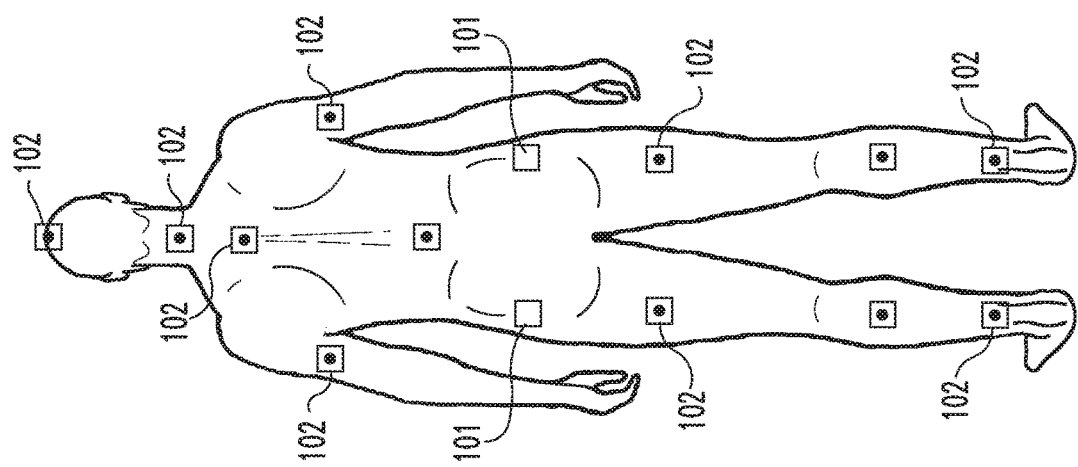
FIG. 3B depicts a second schematic representation of the System of FIG. 1.
Figure 3A:
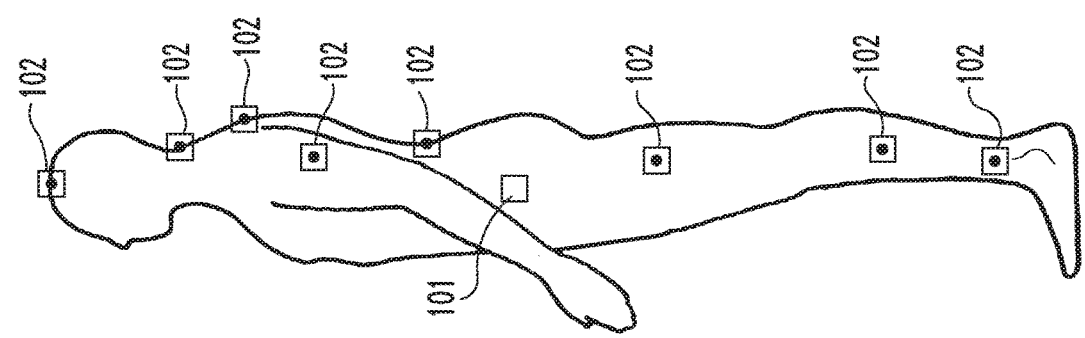
FIG. 3A depicts a first schematic representation of the System of FIG. 1.

FIGS. 3A-3B illustrates a first embodiment of the present, novel system 100 for training users to attain and/or maintain targeted posture and/or other positions for different parts of the body. The training may be provided through signals (i.e., vibration, sound and/or visual alarms and/or alerts) transmitted to a user and/or activated by measured changes in posture and/or position. Those signals are provided by one and/or more sensors 102 and/or in some embodiments a controller 101. Controller 101 typically may be used to program sensors 102 with posture and/or position parameters (e.g., desired vertical and/or horizontal planes, ranges/distances between sensors 102, etc.). In some embodiments, controller 101 may also illustrate posture and/or body position information through a display, typically based on data from sensors 102 and/or historical records. Each sensor 102 may be directly and/or indirectly (i.e., through clothes and/or accessories) attached to and/or worn on a specific part of a user's body. Those parts of the body typically may be selected based on certain activities the user engages in where biofeedback information and/or training may enhance appearance, performance, health and/or safety. Selected activities may be as simple as standing and/or sitting with head held high and back erect; and/or as complicated as skiing with legs shoulder-width apart, knees bent at a fifty degree angle, and hips centered over the ball of the feet; as critical as keeping a head up and staying awake while driving; and/or the like.

Sensors 102 typically may be placed on the body and/or worn. For example, sensors 102 may be located on an individual's back, skull, neck, boot, foot, leg, chest, hip, and/or the like. Depending on the desired monitoring and/or feedback, one or more sensors 102 may form a mesh to inform controller 101 of various parameters of posture, activity, and/or the like.

The sensor detects and/or activates an alarm when a user attains and/or deviates from a targeted posture and/or position by measuring changes in the user's horizontal and/or vertical fields, and/or by wirelessly measuring distances between two and/or more of such devices. For example, if one sensor is attached to a user's right shoulder, and/or a second is attached to a user's left shoulder, controller 101 sets a target position when both shoulders are arched backward. The coordinates for that target position typically may be represented by either or both (x) the distance between the devices and/or (y) the horizontal/vertical planes of each device. If the user slouches forward, the targeted distance may be exceeded and/or planes change; either of which activates an alarm.

Biofeedback information and/or training may be provided via the alarms from sensors 102 and/or in certain embodiments from controller 101. Those alarms typically may be activated when either (x) the user deviates from a preset position and/or posture (which may be adjusted with tolerances so that a deviation typically may be more than a preset degree (e.g., ten, fifteen, thirty, etc. degrees) and/or for more than a preset period of time (e.g., two, five, twenty, etc. seconds, minutes, hours, etc.) before the alarm is activated); and/or (y) the user achieves a preset, targeted position and/or posture. The devices are programmed so that the alarm typically may continue until a deviation is corrected. By way of example, if a user attaches a sensor 102 to his head and/or neck while driving, vibratory and/or audible alarms typically may be activated in that sensor, and/or in certain embodiments controller, if, having fallen asleep, the user's head tilts so as to deviate by more than fifteen degrees in any direction for more than five seconds from sensor's preset vertical plane. As another example, if a skier has sensors 102 on the front and/or back of a ski boot, and on each hip and/or knee, vibratory and/or audible alarms typically may be activated in each sensor and/or controller 101 once the user attains a preset stance with the right and left feet a distance apart (e.g., one-half, one, two, etc. feet) apart, the knees bent at a fifty degree angle, and/or the hips centered over the heels.

Each sensor 102 typically may have a unique digital signal that allows controller 101, through wireless communication link 201, to program settings for that sensor (e.g., sounds, body position targets, permitted deviations, etc.), and/or to distinguish each sensor from others. Controller 101 has unique digital signals that allow it to communicate with each sensor 102. Controller 101 maintains its communication links to each sensor 102 via a BLUETOOTH, infrared, radio and/or like communication system 201.

Figure 4A:
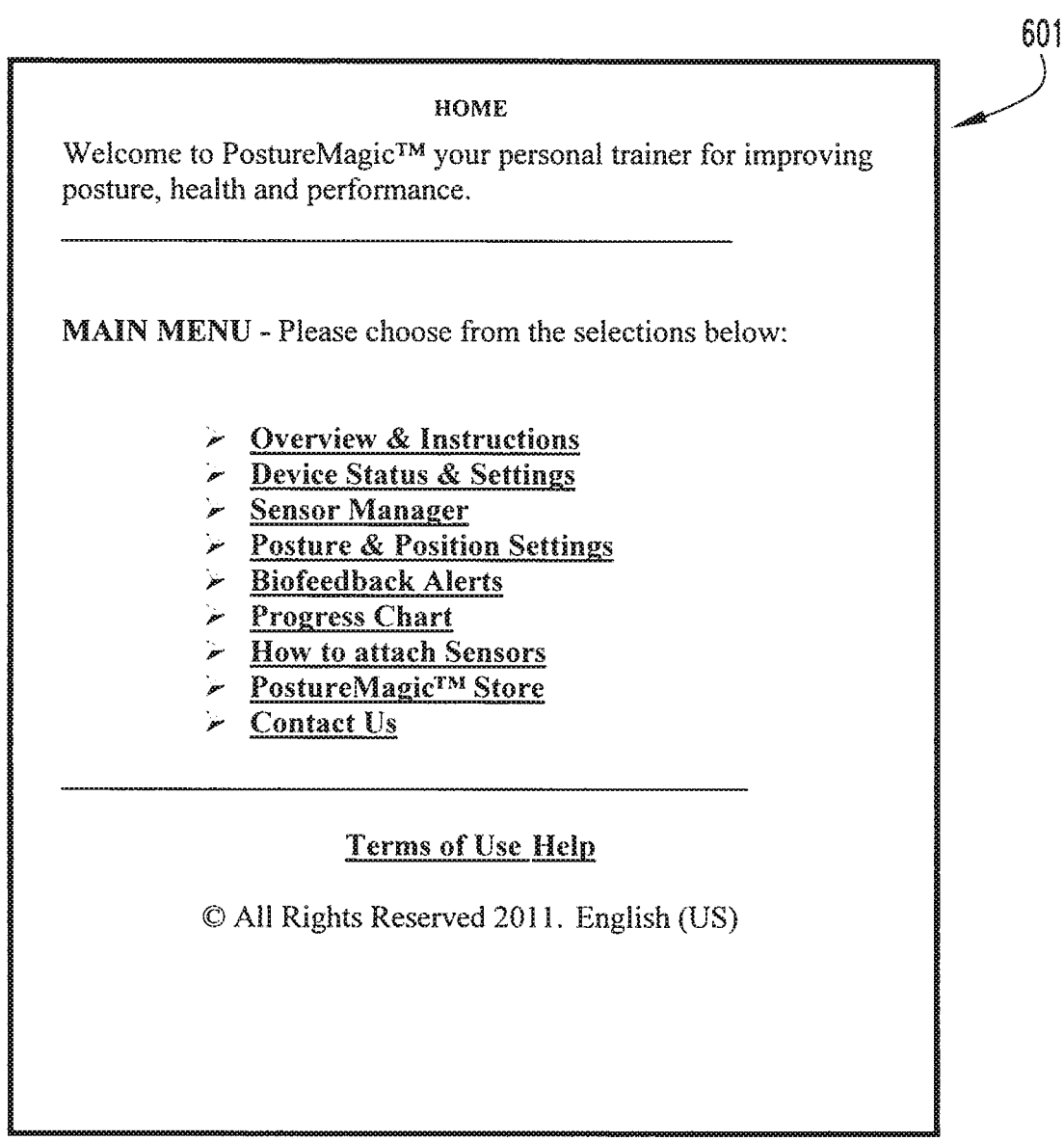
FIG. 4A depicts screenshots for portions of the System of FIG. 1, more specifically a Home page.

FIGS. 4A-4B illustrates one embodiment of a menu system of, and other screenshots for, system 100 that typically may utilize a device on which system software 401 has been installed (e.g., smartphone, PDA, PC, laptop, etc.).

FIG. 4 also illustrates certain functionalities of system 100, and the "look and feel" of system software and/or application 401. It is to be noted that the illustrated menu system and/or screenshots are exemplary only. Other menu systems and/or screenshots/pages may be readily developed and/or provide additional functionalities and/or capabilities.

Home page/main menu 601 typically may be a sample screen/page of system software program/application 401. The menu gives users various options for configuring and/or using system 100 and/or its devices. The selections of subpages accessed through main menu 601 typically are illustrated in 602-608. By clicking on a link to a subpage in main menu 601, that subpage appears on the screen. From any subpage (e.g., 602-608), by clicking on a "Main Menu" link, the user typically may be returned to home page/main menu 601.

System Overview and Instructions screen/page 602 provides the user with brief descriptions of different system 100 components and/or software features. This page typically instructs the user in the operation of system 100 and/or describes its component devices and/or functions. By clicking on any definitional and/or descriptive item highlighted on this page, another subpage opens on the screen with information and/or actions the user may perform.

Depicted on FIG. 5A, device status & settings screen/page 603 typically provides the user with a detailed inventory of sensors 102; the body parts/positions with which the sensors are associated; and/or the sound/vibration settings for the sensors and/or controller 101. The page also allows the user to see the status ("on"/"off") of each sensor, and/or directs the user to modify sensor 102 and/or controller 101 settings and/or add information by clicking on a "Device Manager" link.

For example, sensor "1" may have a status of "On," be located on the user's right shoulder, and have an enabled sound alarm like a bell. Additionally, sensor "3" may have a status of "Off," be located on the user's center upper back, and have a sound alarm like a gong. Device status & settings screen/page 603 may also include settings such as vibration, auditory, and/or visual alarm settings and/or state. There may also be links to modify and/or add sensors 102, which typically may redirect the user to device manager screen/page 604.

Depicted on FIG. 5B, device manager screen/page 604 provides various programming functions to manage system devices. Users typically may set parameters for sensors 102 and/or controller 101. Those parameters typically include (i) activating audible alarms in sensors and/or controller, (ii) selecting a specific audible sound for each sensor, (iii) activating a vibration alarm in controller, (iv) setting permitted deviations from targeted positions, (v) designating the period of time a deviation in position may be permitted to continue before an alarm typically may be activated in a sensor, (vi) assigning a number to each sensor, (vii) associating each sensor with a specific part and/or area of the user's body, and/or the like.

For example, device manager screen/page 604 typically may include settings for user information, which sensors 102 are enabled, how sensor 102 may turn on, turn off, provide alarms, and/or customize alarms (e.g., bell, chime, gong, siren, etc.), where the sensor 102 is located, and/or the like. Alarm conditions for sensor 102 alarms may also be configured. For example, deviation-based alarms and/or achievement-based alarms may be configured. Deviation-based alarms typically may be used where a user may wish to avoid certain postures and/or positions, such as holding a head upright. Deviations, for example, may be configured in distance, percentage of deviation (e.g., 1%, 2%, 10%, 50%, etc.) from an expected position, and/or the like. Similarly, achievement-based alarms typically may be used to train a user to attain a posture and/or position. For example, this may trigger an alarm when you sit upright, allowing the user feedback that he or she is properly oriented. Tolerance with these alarms may also be configured, such that sensor 102 typically may not trigger unless a deviation threshold is exceeded.

Depicted on FIG. 6, posture & position screen/page 605 allows users to program targeted positions and/or postures for sensors 102. From this screen, a user may select a prescribed activity (e.g., standing, sitting, driving, skiing, etc.), which may then open a body avatar on which the user may virtually place one and/or more sensors. With a sensor attached to the user's body, he and/or she may then change positions in order to create a targeted posture and/or pose that may be saved. This page/screen also illustrates permitted deviations from targeted positions. Once a targeted position has been saved, the user may proceed to a biofeedback session, and/or typically may be "trained" by receiving vibration and/or sound and/or visual alarms/alerts whenever he and/or she deviates from, and/or achieves, that target.

Figure 7A:
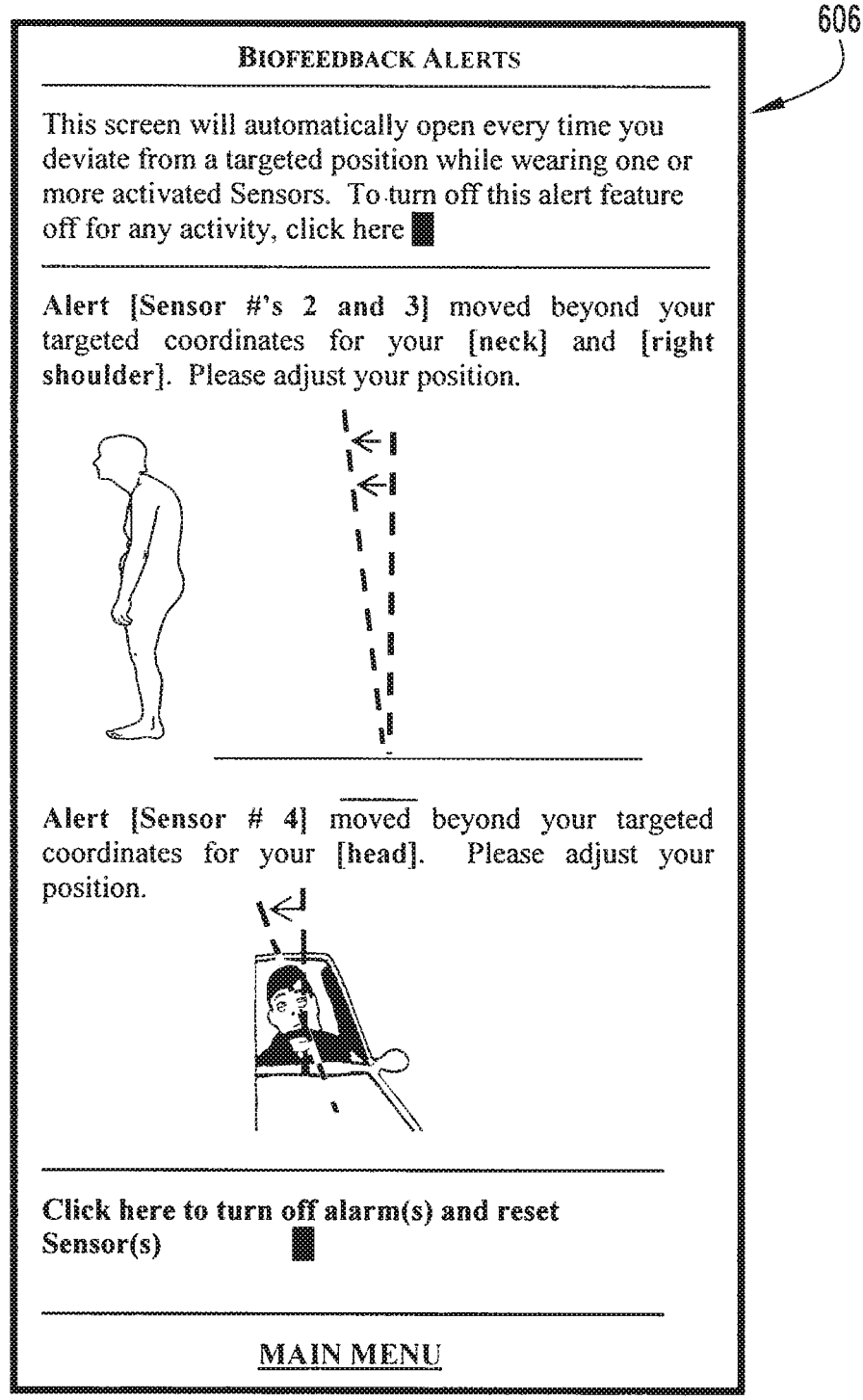
FIG. 7A depicts sample screenshots for portions of the System of FIG. 1, more specifically a Biofeedback Alerts page.

Depicted on FIG. 7A, alerts screen/page 606 provides additional biofeedback information to users. Unless deactivated by a user for an activity, the screen may automatically open each time an alarm typically may be activated by one and/or more sensors 102. The screen typically provides real-time notifications and/or visual displays of deviations from, and/or attainment of, targeted postures and/or positions. Alerts screen/page 606 typically may also allow a system 100 user to turn off alerts, customize alert deviation threshold, reset sensors 102, and/or the like. In some further implementations, selections may be provided for saved activities and/or postures. For example, a user may select from a drop-down list of sports, postures, and/or combinations thereof for one or more body parts to customize and/or set system 100 parameters. In yet further implementations, these saved selections may also enable and/or disable one or more sensors 102 temporarily and/or permanently so as to cease alarms that may otherwise be generated.

Depicted on FIG. 7B, How to Attach Sensors screen/page 607 provides instructions for attaching sensors 102 to parts of the user's body. A user typically may be instructed how sensors 102 should be attached to body parts, clothing, accessories, and/or the like. In some implementations, selecting one or more body parts on How to Attach Sensors screen/page 607 (i.e., by clicking on an image, selecting from a list, and/or the like) may generate one or more instruction routines for attachment to that selection.

Figure 8:
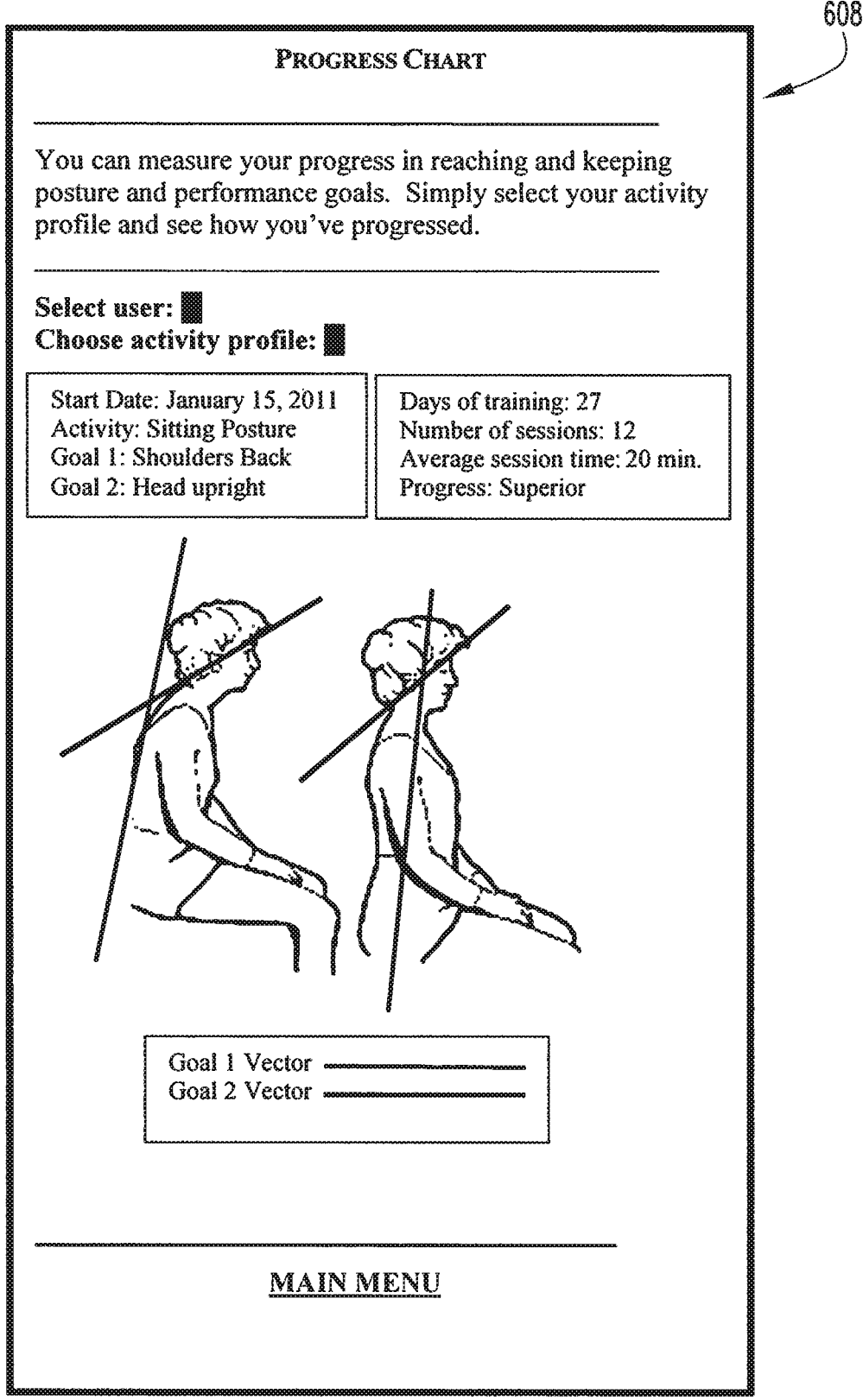
FIG. 8 depicts sample screenshots for portions of the System of FIG. 1, more specifically a Progress Chart page.

As depicted on FIG. 8, Progress Chart screen/page 608 typically may provide historical and/or real-time data to a user about progress in reaching and/or maintaining targeted posture and/or position goals. From this screen/page 608, a user may select the activity he and/or she wishes to monitor, and/or may view a graphic representation of progress in relation to the established target for that activity. For example, a user may be able to view his or her posture history graphically and/or statistically as a series of images, graphic, video, and/or the like. Such display may, in some implementations, allow predictive displays as well. For example, based on a user's progress historically, the system may analyze and calculate to predict (numerically, graphically, and/or the like) how a user will look at a given timeframe and/or when a user may reach a certain posture/position. In certain embodiments, a user may record a real-time representation of posture/position changes during an activity and/or play the recording back to gauge progress.

Figure 9:
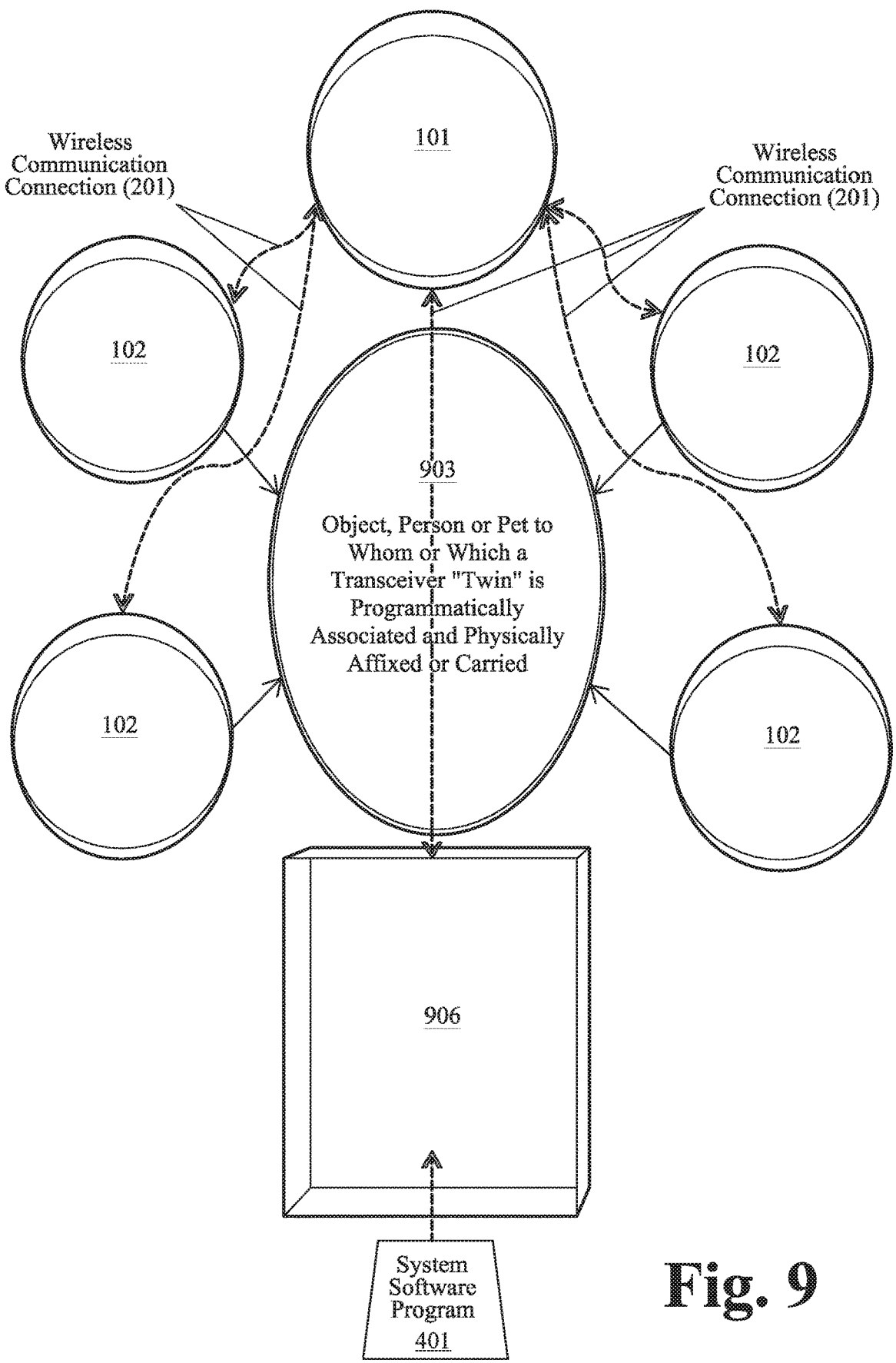
FIG. 9 depicts a high-level diagram of a second implementation of the System.

Another implementation of the present novel technology may be for use as a personal security and location system. FIG. 9 depicts a high-level diagram of this implementation of system 100. FIG. 9 diagrams system 100 and/or its component devices and/or relationships. System 100 includes a controller 101 that uses battery and/or other power sources and/or typically may be programmed to communicate with one and/or more other sensor devices 102 via BLUETOOTH, infrared, radio frequency, audio and/or other technologies 201. Typically, controller 101 typically may be lightweight and/or small such that controller 101 may be easily portable and/or even concealable. For example, controller 101 may typically be kept in a user's pocket and/or worn on a necklace and/or bracelet, and/or as a specially-designed wristwatch. In other implementations, controller 101 may be of waterproof and/or shock resistant design so as to be wearable in a pool, bath and/or shower. Typically, sensors 102 are physically attached to, placed in, on and/or about an object 903. Object 903 may be a thing, a person, and/or a pet. In some implementations, sensors 102 may be affixed to an enclosure containing object 903. In some implementations system 100 may also include one and/or more computer devices 906. In such implementations, one and/or more of one and/or more computer devices 906 may have telecommunication, radio communication, and/or the like capabilities. System software program 401 typically may be installed on computer devices 906.

In other implementations of system 100, controller 101 may include additional sensors, buttons, indicators, and/or the like. For example, described below in this application, a built-in actuator/Panic button that automatically causes a computer device 906 to dial "911" and/or other numbers and/or solicit help may be included with system 100. The volume and/or sound of the audible alarm for controller 101 and/or each sensor 102 (and in certain implementations, a computer device 906) may be set by the user to possess one or more distinguishing sounds and/or volumes.

In operation, controller device 101, having a form of a fob and/or like object typically may be actuated automatically to emit a sound and/or vibration once either (i) a communication link to a sensor 102, which also has the form of a fob and/or like object typically may be broken by virtue of controller 101 and/or sensor 102 being separated from each other by further than a programmable, defined distance and/or range as the result of theft, inadvertence and/or other reasons; and/or (ii) after being separated, controller 101 and/or a sensor device 102 are brought back within the defined distance and/or range of each other. Each sensor 102 typically may have an individualized digital signature recognized by controller device 101 (and in some implementations a computer device 906) through wireless communication system 201 so as to distinguish it from other sensor devices 102 that may be part of system 100. In certain implementations, a computer device 906 may function as a controller 101 and/or sensor 102 (e.g., as disclosed in FIGS. 12 and 13).

The controller 101, and/or in some implementations computer device 906, may set distance and/or range for each sensor 102, and/or if person, object, and/or pet 903 to which sensor 102 typically may be affixed moves beyond that distance and/or range, an alarm (audible and/or vibratory) typically may be set off in controller 101 and/or sensor 102 (and in certain implementations, a computer device 906). System 100 may also be used in reverse so that, by example, if after moving beyond preset distance and/or range, an object, person, and/or pet to which sensor 102 typically may be attached moves back within range of controller, such alarm typically may again be set off in all devices.

The sensors 102 may typically be small (e.g., the size of a quarter and/or half dollar coin), programmable transceivers operated by battery and/or other power source(s). Sensors 102 may be carried upon and/or in an object, person, and/or pet 903 and/or attached through various mechanism, including adhesive backing, an eyelet permitting sensor 102 to be worn on a necklace, bracelet, etc. Each sensor 102 typically may be programmable through its own user interface (and/or in some implementations by controller 101 and/or computer device 906) so as to have a distinct alarm sound and/or volume. When separated from controller 101 by more than a distance and/or range that may be adjustable and/or prescribed by a user, sensor 102, and/or controller 101, and in certain implementations a computer device 906, each emits the distinct alarm sound programmed for such sensor for a fixed period of time. Conversely, once separated by being moved beyond the prescribed distance and/or radius, the alarms typically may again sound in sensor 102 and/or controller 101, and in certain implementations, computer device 906 once sensor typically may be brought back within range of controller (and in certain implementations, computer device 906).

Devices in system 100 typically may communicate with each other using BLUETOOTH, Wi-Fi, radio wave, infrared, and/or other technologies 201. In that way controller 101 and/or one and/or more computer devices 906 may communicate with and/or control the operations of, one and/or more sensors 102, including setting sound alert tones and/or volumes, and/or prescribing distances and/or radiuses governing when alarms are triggered, etc.

Figure 10A:
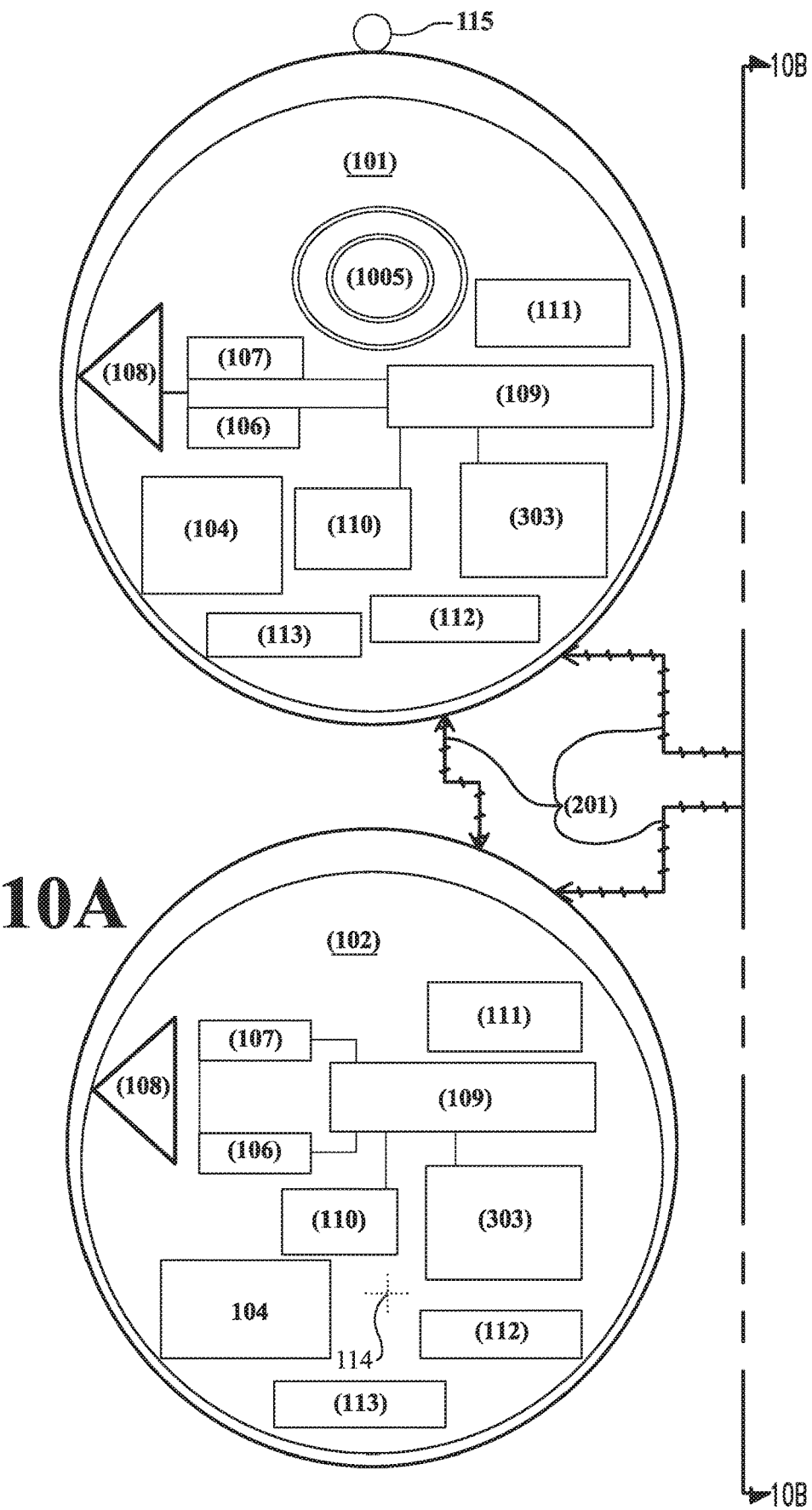
FIG. 10A depicts a first block diagram of certain components of the System of FIG. 9.

FIG. 10A depicts a block diagram of certain components of system 100. FIG. 10 illustrates certain internal components of the devices included in system 100, which are intended to be exemplary only. Controller 101 typically includes a housing (which in certain implementations may be of waterproof design) containing circuitry and/or other components, described below.

In certain implementations, a built-in actuator (Panic button) capable of initiating automated dialing and/or messaging functions in a computer device 906 in the event of emergencies (described below) may be included.

A vibration device 111 typically may be included that causes controller 101 to vibrate as an indicator that a sensor 102 in system 100 has been lost and/or found: that is, it has been moved beyond a preset distance and/or range from controller 101, and/or once out of range, has been brought back within a preset distance and/or range from controller 101.

Circuitry for external data and/or other communications with one and/or more sensors 102 and in certain implementations computer devices 906, including a receiver 107, a transmitter 106, and an antenna 108 typically may facilitate intercommunication between system 100 components. Antenna 108 typically transforms electromagnetic energy to electrical signals provided to receiver 107 and transforms electrical signals from transmitter 106 to electromagnetic energy for transmission to remote radio receivers in one and/or more sensor devices and in certain implementations, one and/or more computer devices 906. Receiver 107 responds to the electrical signals from antenna 108 to produce detected data for supervisor device 109. Receiver 107 may include circuits such as filters and/or demodulators. Transmitter 106 responds to formatted data from supervisor device 109 to provide the electrical signals to drive antenna 108. Transmitter 106 may include circuits such as modulators and/or filters. Antenna 108, receiver 107, and/or transmitter 106 together form a radio communication circuit for two-way radio and/or other wireless communication with remote radio devices such as one and/or more sensors 102, and in certain implementations one and/or more computer devices 906.

Supervisor device 109 typically may act to control the operation of controller 101. Supervisor device 109 may be implemented as a processor, microprocessor, digital signal processor (DSP), and/or any other logic circuit and/or combination of circuits providing control functions. Supervisor device 109 operates in response to data and/or program instructions stored in memory 110. In one mode, supervisor device 109 typically controls radio and/or other wireless communication circuit by directing the tuning, activation, and/or deactivation of the circuit.

An on-off switch 104 typically may act to energize connected circuitry, which in certain implementations may include an LED and/or other indicator to show when controller device 101 typically may be active.

A memory unit and/or device 110 typically may be included that is capable of storing data and/or program instructions for operation of controller 101 and/or other system 100 components.

A user interface 303 typically may allow a user to control controller device 101, which in certain implementations includes a push button, touchscreen, and/or other built-in actuator device to let the user to select programming options for sensor device (e.g., alarm sounds, volume and/or range settings), and/or a display screen sufficiently large to display requisite programming and/or other information for controller 101. In certain implementations, the user interface may enable the user to select programming options for sensors 102 (e.g., alarm sounds and/or range settings). In still other implementations, user interface 303 may be obviated and/or omitted.

A battery and/or other power source 113 typically may be included to provide sufficient power to operate controller 101 and/or facilitate mobility.

A speaker and/or other sound system 112 capable of emitting a variety of sounds (e.g., siren, beep, whistle, gong, etc.) to indicate that a sensor 102 has deviated beyond a certain threshold typically may allow system 100 to announce separation distance(s) being exceeded. In certain implementations, controller 101 may include and/or or be replaced by computer device 906. Speaker 112 may, in some implementations, also energize after sensor 102 is brought back within a preset distance and/or range.

Mechanisms for attaching controller 101 and/or sensor 102 may be included, such as eyelet 115 and/or similar construction and/or attachments to the housing through which a chain, ring, etc. may be inserted so as to enable a user to easily carry controller 101 on a keychain and/or wear it on a necklace and/or bracelet. In certain implementations, controller device 101 may also take the form of, and/or be incorporated into, a wrist watch and/or worn on the wrist through a watch band device.

As also shown in FIG. 10, each sensor 102 typically may include a housing containing circuitry and/or other components that may include the following:

Circuitry for external data communication with controller device 101, and certain implementations one and/or more computer devices 906, including a receiver 107, a transmitter 106, and/or an antenna 108. Antenna 108 typically transforms electromagnetic energy to electrical signals provided to receiver 107, and/or transforms electrical signals from transmitter 106 to electromagnetic energy for transmission to remote radio receivers in controller device 101 and/or in certain implementations one and/or more computer devices 906. Receiver 107 typically responds to the electrical signals from antenna 108 to produce detected data for supervisor device 109. Receiver 107 may include circuits such as filters and/or demodulators. Transmitter 106 typically responds to formatted data from supervisor device 109 to provide the electrical signals to drive antenna 108. Transmitter 106 may include circuits such as modulators and/or filters. Antenna 108, receiver 107, and/or transmitter 106 typically together form a radio communication circuit for two-way radio and/or other wireless communication with remote radio devices such as controller 101, and in certain implementations one and/or more computer devices 906.

Vibration device 111 that typically may cause sensor 102 to vibrate as an indicator that the associated sensor 102 has been lost and/or found; that is, it has been moved beyond a preset distance and/or range from controller 101, and/or in certain implementations, a computer device 906; and/or once out of range, has been brought back within a preset distance and/or range from controller 101 and/or computer device 906 as the case may be.

Supervisor 109 that typically may control the operation of sensor 102. Supervisor device 109 may be implemented as a processor, microprocessor, digital signal processor (DSP), and/or any other logic circuit and/or combination of circuits providing control functions. Supervisor device 109 typically operates in response to data and/or program instructions stored in memory 110. In one mode, supervisor device 109 typically controls the radio and/or other wireless communication circuit by directing the tuning, activation, and/or deactivation of the circuit.

Memory unit and/or device 110 that typically may be capable of storing data and/or program instructions for use with system 100 and/or sensor 102.

A user interface 303 that lets a user control sensor 102 and in certain implementations, includes a pushbutton, touchscreen, and/or other built-in actuator device to let the user to select programming options for sensor device 102 (e.g., alarm sounds, volume and/or range settings), and/or a display screen sufficiently large to display requisite programming and/or other information for sensor 102. In some implementations, user interface 303 may be omitted and/or obviated from sensor 102.

An on-off switch 104, which in certain implementations may include an LED and/or other indicator to show when sensor 102 typically may be active.

A battery or other power source 113 that may provide power sufficient to operate sensor 102.

A speaker and/or other sound system 112 that is capable of emitting a variety of sounds (e.g., siren, beep, whistle, gong, etc.) to indicate that sensor 102 has been lost and/or found (i.e., has been moved beyond a preset distance and/or range from controller 101, and/or in certain implementations a computer device 906; and/or once out of range, has been brought back within a preset distance and/or range from controller 101 and/or computer device 906 as the case may be).

Mechanisms for attaching controller 101 and/or sensor 102 may be included, such as eyelet 115 and/or similar construction and/or attachments to the housing through which a chain, ring, etc. that may be inserted so as to enable a user to easily carry sensor 102 on a keychain and/or wear it on a necklace and/or bracelet. Sensors 102 may also have adhesive, hook-and-loop type fasteners, and/or similar backing systems to allow the same to be affixed to objects.

Figure 10B:
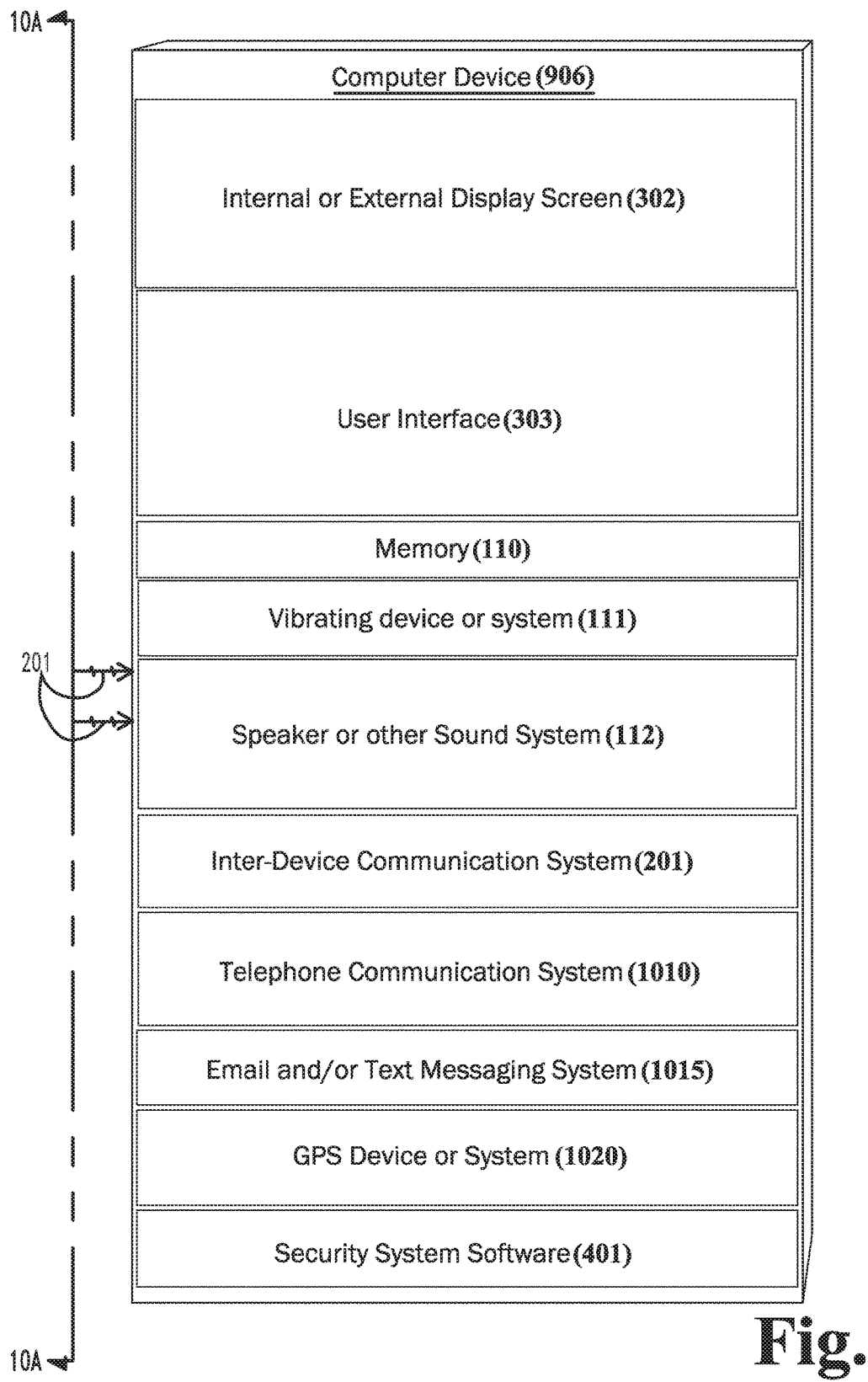
FIG. 10B depicts a second block diagram of an example computer device associated with the System of FIG. 9.

As also shown in FIG. 10B, system 100 may include one and/or more computer devices 906 that have been programmed with software program 401 for system 100. Computer devices 906 may include a programmable cell phone (e.g., smartphone), PDA, and/or other handheld computer pad, tablet and/or similar device with telephone/email functionality, and in certain implementations may also include a desktop and/or laptop computer. Each computer device 906 has a construction, circuitry, operating system, email, text messaging and/or other software, processing and/or other features and abilities typically found in "off-the-shelf" products in the marketplace, including:

A display/monitor screen 302 and/or monitor enabling a user to view menu options, obtain information about and/or program controller 101 and/or sensors 102. Screen 302 may, in some implementations, display System 100 information such as, but not limited to, each controller 101 and/or sensor 102; status (e.g., armed, disarmed, etc.) of each System 100 device; the object 903 associated with each device; device programming options (e.g., alarm sounds, range, alert recipients, 911 messaging, etc.); purchasing and/or contact information; and/or the like User interface 303 to let user control computer device 906, which in typical implementations, may include a (a) keypad, touchscreen and/or other device for entering data and/or initiating actions, (b) a display screen, (c) a microphone and/or speaker, and/or the system software 401 and/or one and/or more other software application programs for controlling the computer device 906 and/or other devices, processing received data, and/or producing a display based on the data. In the particular exemplary implementation described herein user interface 303 may include a display screen 302 sufficiently large to display graphical and/or other data and/or text, and/or modalities for enabling a user to input information, make selections, create messages for automated delivery, and/or perform other tasks relevant to the operation of system 100.

User interface 303 typically may allow a user to enter data and/or perform programing functions such as, but not limited to, setting the range, alarm sounds and other functions of System 100 device; entering user and/or third-party contact information and/or other data for emergency notifications; creating voice, text, and/or email message content for automated alerts; setting device sound, dialing sequence, and/or other response/operating parameters for panic button 1005 operation.

Memory unit 110 capable of storing data, messages, program instructions and/or other information associated with the operation of system 100. Memory 110 may also store system software 401 and/or like data.

In certain implementations vibration device 111 may be included that causes computer device 906 to vibrate as an indicator that controller 101 and/or sensor 102 in system 100 has been lost and/or found (i.e., has moved beyond a preset distance and/or range, and/or is brought back within a preset distance and/or range).

Speaker and/or other sound system 112 capable of emitting a variety of sounds (e.g., siren, beep, whistle, gong, etc.) to indicate that controller 101 and/or sensor 102 in system 100 has been lost and/or found (i.e., has moved beyond a preset distance and/or range, and/or is brought back within a preset distance and/or range). Speaker 112 may also sound a siren or other alarm if panic button 1005 is actuated and/or may initiate certain sound/dialing silencing functions based on panic button 1005 response settings.

Circuitry and functionality 201 for external data communication with network devices so as to permit communication with controller 101 and/or sensors 102. Communications may be either or both wired (e.g., USB, IEEE 1394, etc.) and/or wireless methods and/or devices (e.g., BLUETOOTH, and/or IEEE 802.11 and/or related standards, and/or other radio wave and/or wireless protocols). In certain cases the computer device 906 may utilize a network interface (e.g., a digital modem and/or transceiver circuit for digital data communication) to link computer device 906 with controller 101 and/or sensors 102.

Alternatively, the network interface may be an entirely wireless circuit of any suitable type for wireless communication, as described elsewhere in this application. Wireless interface 201 may communicate according to a wireless protocol (e.g., BLUETOOTH, IEEE Standard 802.11 and/or related standards, and/or cellular and/or like transceiver circuits). Also, circuits which communicate using unlicensed frequency bands may be used for data communication among system devices.

Telephone communication system 1010 for automatically dialing "911" and/or placing other calls, and/or playing prerecorded messages to designated recipients based on loss and/or theft of a sensor 102 and/or controller 101, and/or a user pressing a panic button 1005.

Email and/or text messaging system 1015 for automatically delivering preprepared messages to designated recipients based on loss and/or theft of a sensor 102 and/or controller 101, contacting emergency services, and/or a user pressing a panic button 1005.

GPS Device and/or System 1020 for ascertaining user location and in certain circumstances, automatically transmitting that location to emergency services and/or other third parties based on loss and/or theft of a sensor 102 and/or controller 101, and/or a user pressing a panic button 1005.

Software application programs and system software 401 to enable computer device 906 to perform conventional operating functions and/or the novel functions of system 100; process received data; and/or produce a display based on the data. System software and/or application 401 may be configured as computer readable program code and/or stored in device's memory 110.

Figure 11A:
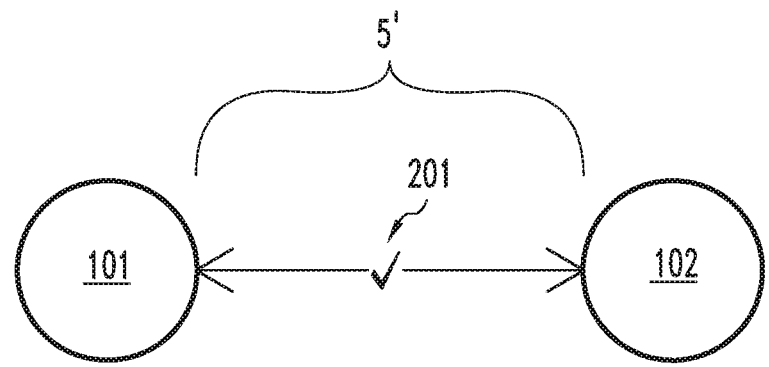
FIG. 11A depicts a first functional schematic representation of the System of FIG. 9 with a controller and sensors in operating range.
Figure 11B:
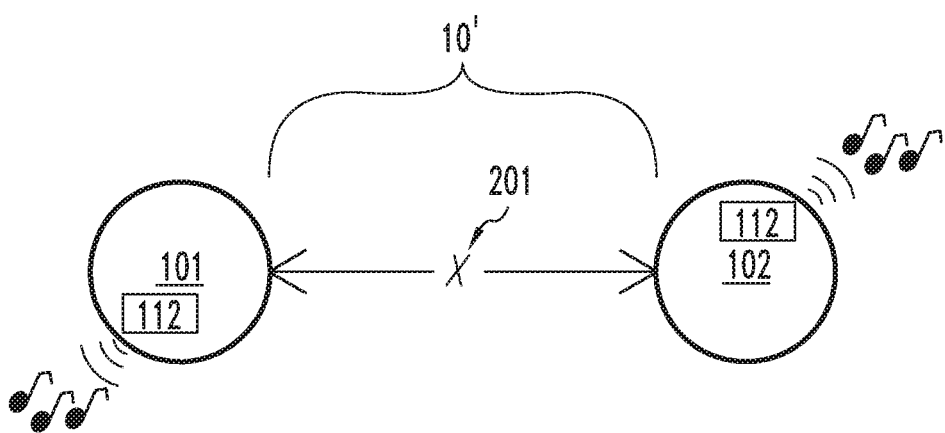
FIG. 11B depicts a second functional schematic representation of the System of FIG. 9 with a controller and sensors beyond operating range with triggered alarm.
Figure 11C:
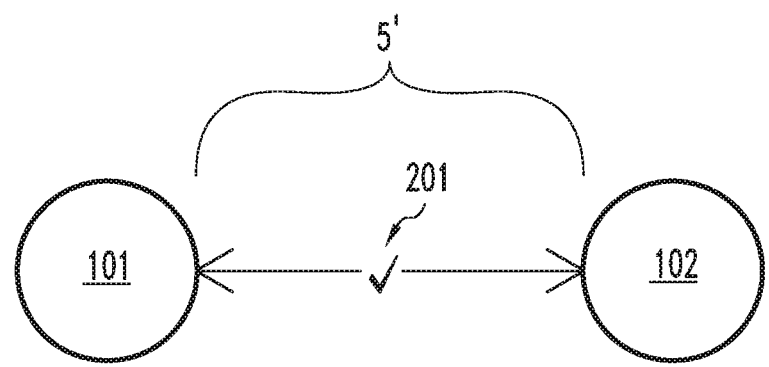
FIG. 11C depicts a third functional schematic representation of the System of FIG. 9 with a controller and sensors returned to operating range.

FIGS. 11A-11C illustrate a first implementation of the present, novel system 100 system for automatically initiating an audible and/or vibratory alert in a first transceiver device, controller 101, and/or one and/or more second sensor devices 102. Alerts may be triggered in one of two ways: (i) the devices are separated from each other by a predetermined distance and/or range (such as through theft and/or oversight); and/or (ii) the devices are brought back within a predetermined distance and/or range of each other after having been separated. FIG. 11A depicts controller 101 and sensor 102 connected at a distance of approximately five feet over wireless connection 201; FIG. 11B depicts the same controller 101 and sensor 102 having a broken connection 201 after exceeding a preset distance threshold (e.g., eight feet) and sounding alarm from speakers 112; FIG. 11C depicts the same controller 101 and sensor 102 again reconnected via connection 201 and having silenced alarming speakers 112.

Each sensor device 102 in system 100 may have a unique sound so as to distinguish it from other sensor devices 102. The same sound programmed for sensor device 102 typically may be also programmed to play in controller 101 to alert a user that a particular sensor device 102 has been lost and/or found. System's sensors 102 may be attached, affixed, inserted into, and/or worn on an object, person, and/or pet 903. Each sensor device 102 has a unique digital signal that allows controller device 101, through wireless communication link 201, to distinguish that sensor device 102 from others. Controller device 101 has unique digital signals that allow it, through wireless communication link 201, to communicate with each sensor device 102 in system 100 (i.e., a distinct signal tuned to each sensor device 102).

Controller device 101 maintains a communication link via a BLUETOOTH, infrared, radio and/or like short-range communication system 201 with one and/or more sensors 102. Sensor 102 may be preprogrammed and/or programmed by a user via device's user interface 303 and/or other internal mechanism, and/or via controller device 101 by a communication link 201) to (i) generate a distinct sound that distinguishes it from other sensor devices 102 in system 100, and (ii) to have a set distance and/or range from controller, so that if it moves beyond that range and/or distance, alarms typically may go off in sensor 102 and/or controller 101. Controller device 101 may be programmed as well so that its alarm sound typically may be identical to the alarm sound of each sensor device 102.

When controller 101 and sensor 102 in system 100 are separated by more than a preset distance and/or range, alarms may be triggered in each device. For example, if a sensor 102 with a certain range (e.g., one, two, three, five, ten, etc. feet) is placed inside a user's wallet and a controller 101 is in the user's front pocket, vibration and/or audible alarms may go off in sensor 102 and/or controller 101 if a pickpocket were to take the wallet beyond the certain range from the owner's pocket, and/or if the user were to leave the wallet on a table and walk out of a restaurant. The alarms may continue for a preset period of time (e.g., five minutes) and then may discontinue; but may be reactivated if controller 101 and/or wallet with sensor 102 were brought back within the communication range of the devices (e.g., ten, one hundred, one thousand feet, etc.). In some implementations, activation and/or deactivation of alarms may be manually activated by user.

System 100 may include numerous sensors 102 (e.g., two, five, ten, one hundred, etc.), each of which may function in the same manner with respect to triggering alarms when moving beyond, and/or back into, a preset distance and/or range from controller device 101. Controller 101 typically may be programmed to distinguish each sensor 102 by its special digital signature (e.g., frequency) and to communicate a separate digital signal to each sensor device 102 linked to controller 101 through wireless communication system 201. Controller 101 typically may store a unique alarm sound for each sensor 102 (e.g., gong, bell, siren, etc.) and/or play that alarm sound if sensor 102 moves out of, and/or back into, the preset distance and/or range. Controller 101 typically may intermittently play the unique alarm sound for each if more than one sensor 102 at a time is moved out of the preset distance and/or range, and/or brought back within that distance and/or range.

Figure 12A:
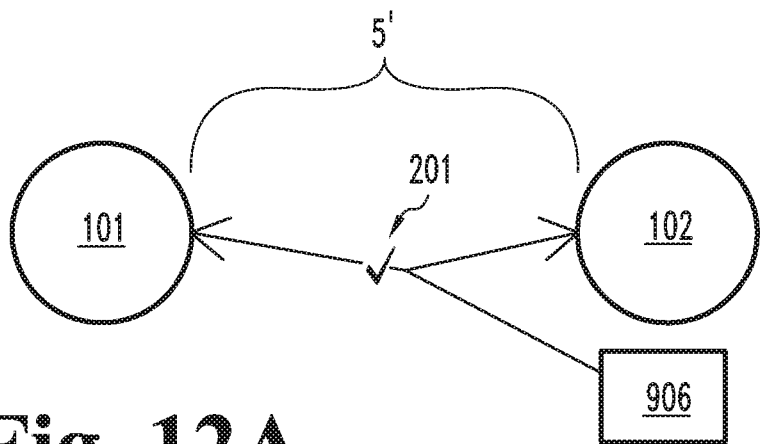
FIG. 12A depicts a schematic demonstrating the functionality of the System of FIG. 9 with a controller, sensor(s), and computer device in operating range.
Figure 12B:
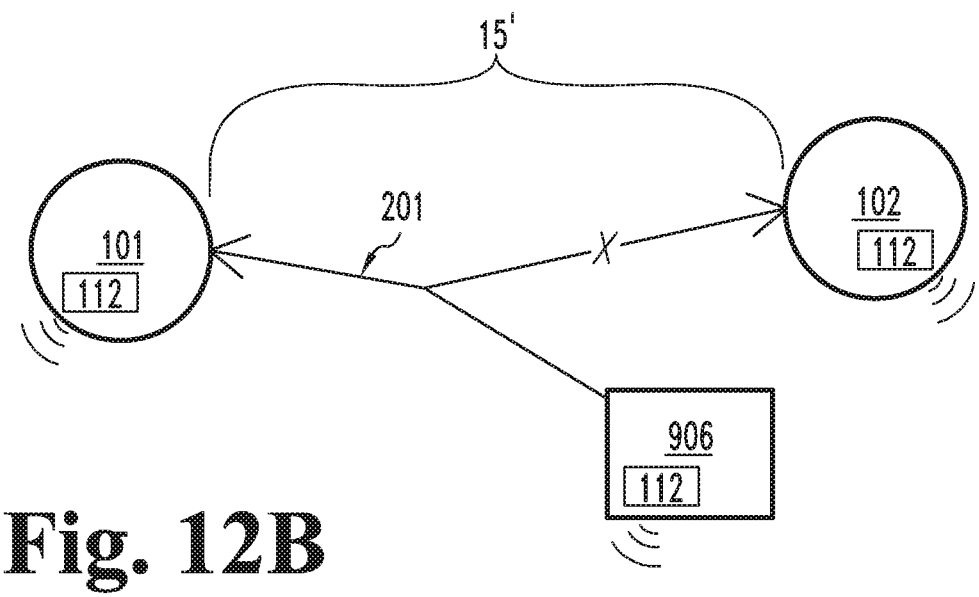
FIG. 12B depicts a schematic demonstrating the functionality of the System of FIG. 9 with a controller, sensor(s), and computer device beyond operating range, triggering all alarms.
Figure 12C:
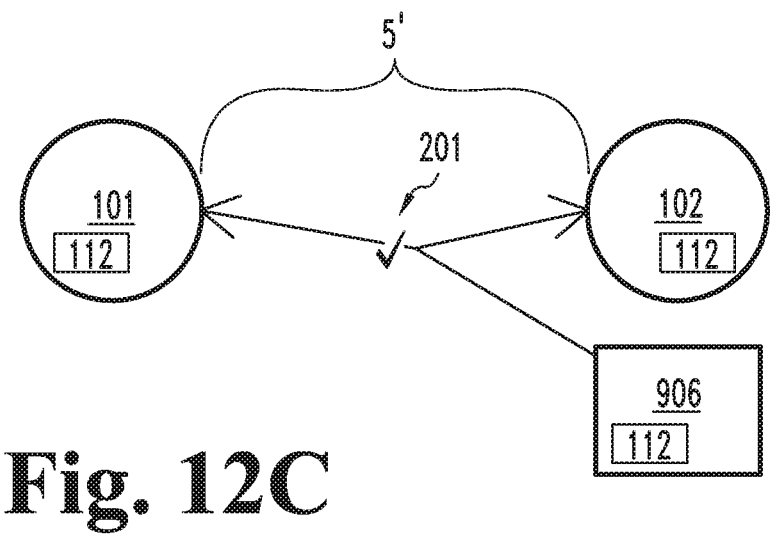
FIG. 12C depicts a schematic demonstrating the functionality of the System of FIG. 9 with a controller, sensor(s), and computer device returned to operating range.

FIGS. 12A-12C illustrate a second implementation of the present novel technology underlying system 100. That implementation incorporates a computer device 906 into system 100 as one of sensor devices 102. System 100 includes a controller 101 that communicates with one and/or more sensors 102, including a computer device 906, via a BLUETOOTH, infrared, radio and/or like short-range communication system 201. Typically, controller 101 and/or sensor 102 and related computer device 906 include built-in alarm systems to vibrate and/or play a distinct sound alerting a user as to when (i) controller 101 and/or sensor 102 (which in this implementation includes a computer device 906) have been separated by more than a programmable distance and/or range from each other; and/or (ii) after having been separated for more than a defined period of time (e.g., one, five, ten, twenty, etc. minutes), are brought back in a programmable distance and/or range of each other.

FIG. 12A depicts controller 101 connected to sensor 102 and computer device 906 via wireless connection 201 at a distance of approximately five feet. FIG. 12B depicts the same controller 101, sensor 102, and computer device 906; however, sensor 102 is now fifteen feet from controller 101 and beyond the preset distance threshold (e.g., ten feet for a time threshold of five seconds), triggering speakers in all three devices to sound alarms. FIG. 12C depicts the same controller 101, sensor 102, and computer device 906 having been brought back into the preset distance threshold, thus silencing the speakers 112.

With system software 401 installed in it, computer device 906 establishes a communication link via a BLUETOOTH, infrared, radio and/or like short-range communication system 201 with controller device 101, which in turn may maintain a communication link 201 with one and/or more sensors 102 in system 100, including computer device 906. Range, alarm sounds, and/or other settings for controller 101, sensors 102, and/or computer device 906 may be internally programmed by user interfaces in each device, and/or through controller 101 and/or computer device 906 via wireless communication system 201.

Computer device 906 typically establishes a communication link 201 with a controller device 101 and in some implementations may program controller device 101 to set the range, alarm sounds, volume, and/or other settings for each sensor 102 in system 100. Computer device 906 functions as a sensor device 102 as well. When controller 101 and/or computer device 906 are separated by more than a preset distance and/or range, identical alarms may be triggered in both devices. The alarms include vibration in each device and/or a distinct alarm sound that identifies computer device 906 (e.g., siren, gong, fog horn, bell, etc.). The same alarm sound that is programmed to issue from computer device 906 may also issue from controller 101 as well. Once controller 101 and/or computer device 906 are separated by more than the preset range, the alarms in each device continue to sound for a predetermined period of time (e.g., one, five, ten, twenty, etc. minutes) and/or until the devices move beyond their communication range (e.g., one, ten, one hundred, one thousand, etc. feet); after which, each device may silenced. If, after being separated for more than the prescribed time period and/or distance controller 101 and/or computer device 906 are brought back within range, the alarms typically may again ring for the preset period of time. In this way, a user may be alerted when computer device 906 and/or controller device 101 is lost and/or found. In addition and as with controller 101, computer device 906 vibrates and/or issues a distinct alarm sound for each sensor device 102 when that device is lost and/or found.

System 100 may include numerous sensor devices 102, each of which may function in the same manner with respect to separation from controller 101. Controller 101 and/or computer device 906 may be each programmed to distinguish each sensor 102 by its digital signal (e.g., frequency), and/or play the sensor 102's unique sound (e.g., gong, bell, siren, etc.) when it is lost and/or found. Controller 101 may be also programmed to communicate a separate digital signal that may be recognized by each sensor device 102 linked to controller 101 through wireless communication system 201. Controller 101 typically may store a unique alarm sound for each sensor device 102 (e.g., gong, bell, siren, etc.) and/or play that alarm sound if sensor 102 moves out of, and/or back into, the preset distance and/or range. Controller 101 typically may intermittently play the unique alarm sound for each if more than one sensor device 102 at a time is moved out of the preset distance and/or range, and/or brought back within that distance and/or range.

FIGS. 13A-13D illustrate a third implementation of the present novel technology underlying system 100. That implementation replaces controller 101 device with computer device 906. With system software 401 installed, computer device 906 establishes a communication link 201 via a BLUETOOTH, infrared, radio and/or like short-range communication system 201 with all sensors 102 in system 100, and in some implementations may program their range, alarm sounds, volume and/or other settings.

Figure 13A:
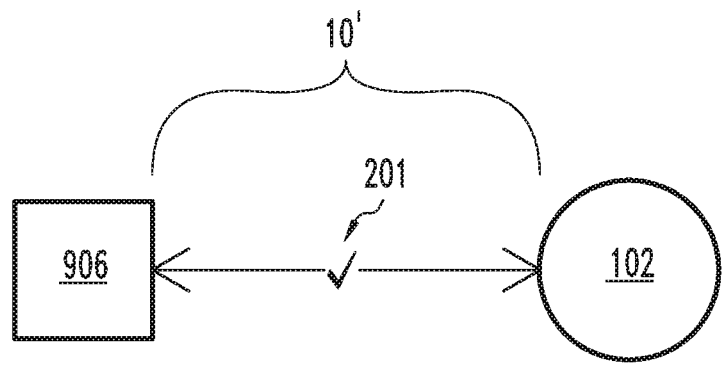
FIG. 13A depicts a schematic demonstrating the functionality of the System of FIG. 9 with a computer device and sensor(s) in operating range.
Figure 13B:
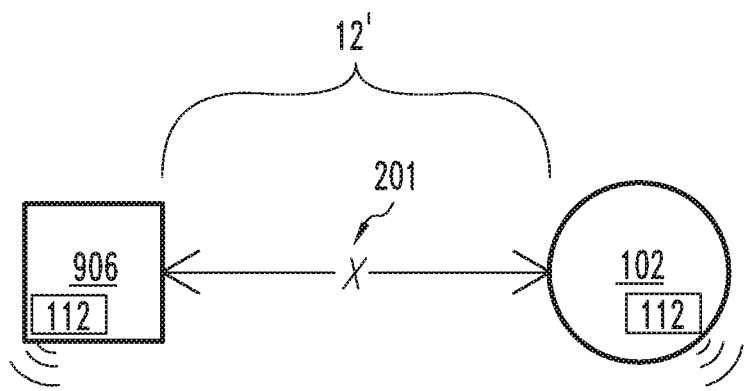
FIG. 13B depicts a schematic demonstrating the functionality of the System of FIG. 9 with a computer device and sensor(s) beyond operating range, triggering alarms in both devices.
Figure 13C:
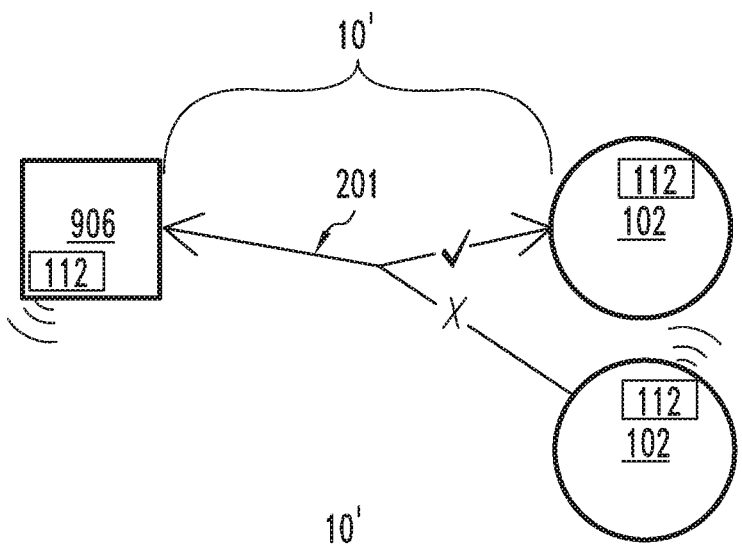
FIG. 13C depicts a schematic demonstrating the functionality of the System of FIG. 9 with a computer device and sensors with one sensor beyond operating range, triggering alarms in computer device and out-of-range sensor.
Figure 13D:
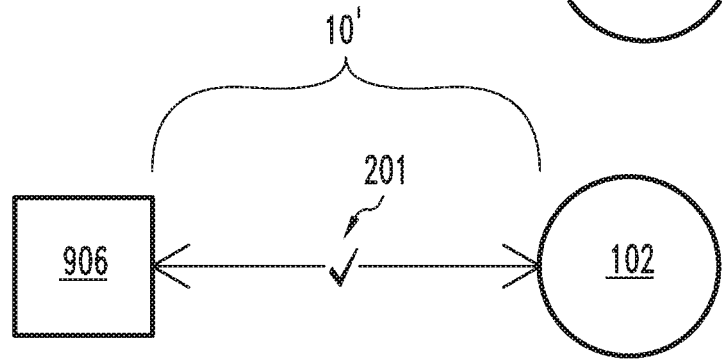
FIG. 13D depicts a schematic demonstrating the functionality of the System of FIG. 9 with a computer device and sensor(s) returned to operating range.

FIG. 13A depicts computer device 906 connected to sensor 102 via connection 201 at a distance of approximately ten feet. FIG. 13B depicts the same computer device 906 no longer connected to sensor 102 via connection 201 at a distance of approximately twelve feet, having exceeded distance threshold (e.g., ten feet for a time threshold of one minute) and thus triggering speakers 112 to play alarms. FIG. 13C depicts the same computer device 906 and sensor 102 joined by a second sensor 102, where the first sensor 102 at a distance of ten feet to computer device 906 has not exceeded the distance threshold and is not sounding alarm, but where the second sensor 102 at a distance of twenty feet is exceeding the distance threshold and causes speakers 112 in computer device 906 and second sensor 102 to sound alarms. FIG. 13D depicts computer device 906 and sensor 102 brought back into the distance threshold and silencing the alarms from speakers 112.

As illustrated in FIGS. 13A-13D, when computer device 906 and/or a sensor 102 are separated by more than a preset distance and/or range, identical alarms may be triggered in each device. The alarms include vibration in each device and/or a distinct alarm sound for each sensor device 102 (e.g., siren, gong, fog horn, bell, etc.). The same alarm sound that may be programmed to issue from a sensor 102 issues from computer device 906 as well. Once computer device 906 and/or sensor device 102 are separated by more than the preset range, the alarms in each device continue to sound for a predetermined period of time (e.g., one, five, ten, twenty, etc. minutes); after which, each device may be silenced. If, after being separated for more than the prescribed time period, computer device 906 and/or sensor 102 are brought back within range, the alarms typically may again go off and/or play for the preset period of time (e.g., one, five, ten, twenty, etc. minutes). In this way, a user may be alerted when a sensor 102 and/or computer device 906 is lost and/or found. If computer device 906 is lost and/or taken, and/or is later found (i.e., brought back within range), vibration and/or auditory alarms sound in all of sensors 102.

Figure 14A:
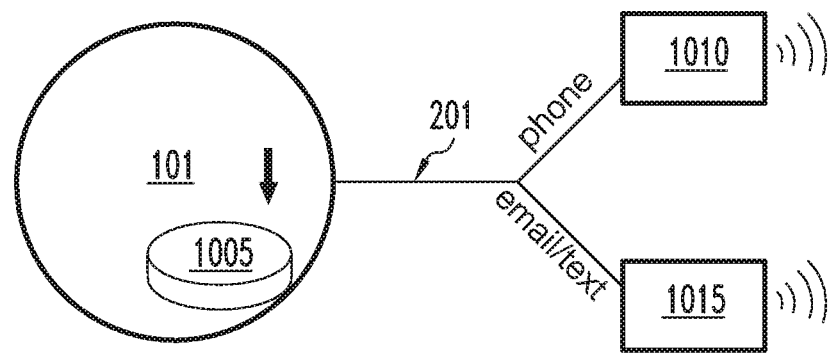
FIG. 14A depicts a schematic demonstrating the functionality of the System of FIG. 9 with a controller having a built-in panic button/actuator device configuration that may initiate distress calls and/or messages to emergency services and/or third parties.
Figure 14B:
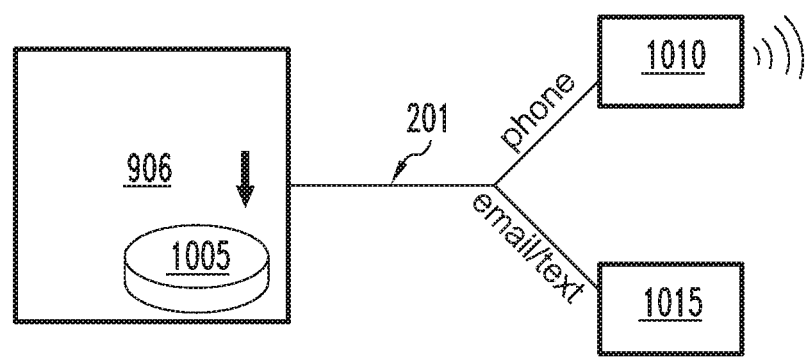
FIG. 14B depicts a schematic demonstrating the functionality of the System of FIG. 9 with a computer device having a built-in panic button/actuator device configuration that may initiate distress calls and/or messages to emergency services and/or third parties.

FIGS. 14A-14B illustrate a fourth implementation of the present novel technology underlying system 100 that may include all of the functions for the system 100 illustrated in this application, and also includes a built-in actuator device/Panic button 1005 as part of controller device 101. Operationally, by pressing the panic button 1005, a user may automatically cause a handheld computer device 906 to dial "911" for help and/or send distress messages in emergency situations even if the user typically may be unable to physically access computer device 906. Pressing the panic button 1005 a specified number of times automatically causes computer device 906 to dial 911 and/or send a prerecorded message requesting a specific type of assistance (e.g., 1 click=police assistance; 2 clicks=emergency medical services (EMS) assistance; and/or 3 clicks=fire rescue assistance). In some implementations, if a user continuously presses the actuator/panic button 1005, a siren and/or other alarm sound may be played from controller 101 and/or computer device 906. The user may cancel a distress call by pressing the actuator/panic button 1005 a preset number of times (e.g., 4 clicks).

As also illustrated in FIG. 14, system 100 may be configured so that certain 911 calls dial silently and/or turn off sounds from computer device's 906 speakers 112 so as not to alert an assailant and/or intruder that a distress call typically may be being placed. In addition to 911 messages, computer device 906 may be programmed to send messages (e.g., email, text, etc.) to third parties after an automated 911 call is placed. In further implementations, system 100 may activate GPS devices 1020, activate microphones and/or other capture device of sensor 102 and/or computer device 906, and/or send preprogrammed messages for locating sensor 102 and/or computer device 906 (e.g., email Internet Protocol (IP) address, GPS location, closed wireless access point, etc.).

FIG. 14A depicts controller 101 having button 1005 thereon and connected to telephone device 1010 and email/text device 1015. Upon activation of button 1005, controller 101 may cause a phone call and/or message through telephone device 1010 (e.g., distress call to emergency services) and/or a message (e.g., email, text, picture, etc.) to be sent to one or more recipients via email/text device 1015. FIG. 14B depicts computer device 906 having button 1005 replacing controller 101 but still connected to telephone device 1010 and email/text device 1015. FIG. 14B depicts only a phone call being triggered through telephone device 1010, but any combination of events may be triggered and/or programmed to occur via button 1005 actuation and/or multiple actuation.

Figure 15A:
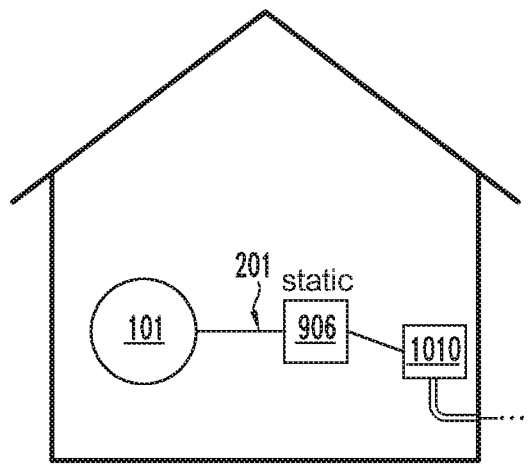
FIG. 15A depicts a schematic demonstrating the functionality of the System of FIG. 9 with a controller having a panic button and a static computer device connected to a landline communication service.
Figure 15B:
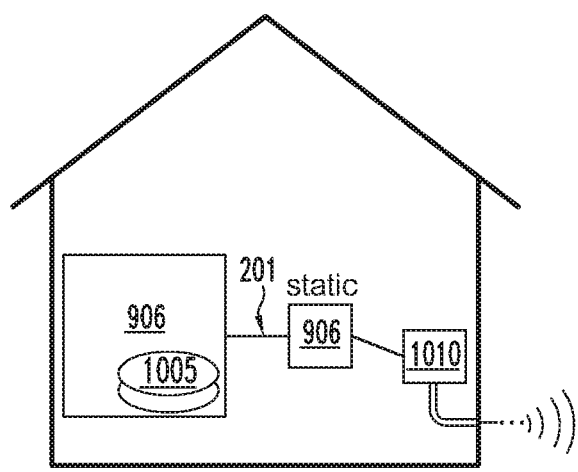
FIG. 15B depicts a schematic demonstrating the functionality of the System of FIG. 9 with a first, handheld computer device having a panic button and a second, static computer device connected to a landline communication service communicating with third-parties and/or emergency services.
Figure 15C:
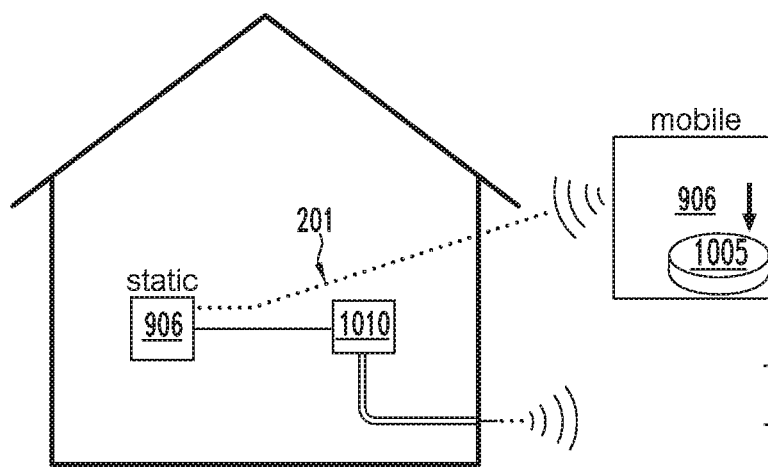
FIG. 15C depicts a schematic demonstrating the functionality of the System of FIG. 9 with a first, mobile computer device having a panic button communicating with a landline communication service via a second, static computer device.

FIGS. 15A-15C illustrates a fifth implementation of the present novel technology underlying system 100 that may include all of the functions for system, but includes the use of a fixed-location computer device 906, such as a home and/or office PC and/or laptop with telephone and/or email functionality. Operationally, by pressing actuator/Panic button 1005 on controller device 101 in wireless network 201, a user may automatically cause computer device 906 in a home, office and/or other fixed location with telephone communication capabilities via telephone device 1010 to dial for help in an emergency. This implementation may also integrate a mobile computer device 906 into system 100 to similarly respond to panic button 1005 when the user is outside of a static location. As illustrated in FIG. 15, the devices in system 100 may perform all and/or substantially all of the functions, and/or have substantially all of the features noted elsewhere in this application, including the ability to automatically dial "911" and/or send prerecorded messages in the event of an emergency by pressing controller's panic button 1005.

When controller 101 is out of range of the stationary computer 906 (e.g., when the user leaves the home area network and/or is mobile), handheld computer device 906 may act as the communication interface for initiating "911" and/or other calls and/or sending alerts. If handheld computer device 906 and/or stationary computer device 906 are both turned "on" and/or within range of controller 101, the closest computer device 906 typically may initiate "911" dialing and/or notification alerts. Integration of fixed location computer device 906 and/or a handheld computer device 906 enables the handheld computer device 906 to interact with and/or respond to controller 101 when the handheld device 906 is at a fixed location (e.g., a home and/or office) and/or while the user is out of range of fixed-location computer device 906. Similarly, static computer device 906 and/or handheld computer device 906 may provide "lost and found" functions by monitoring one and/or more sensors 102 in the home and/or on the go.

FIG. 15A depicts controller 101 connected over wireless connection 201 to static computer device 906, which is in turn connected to telephone device 1010 and landline telephone service (e.g., twisted pair copper telephone, VOIP, etc.). FIG. 15B depicts another computer device 906 (mobile and/or static) with button 1005 connected to static computer device 906, which is in turn connected to telephone device 1010. Upon activation of button 1005, static computer device 906 is signaled to send one or more messages to one or more recipients over the landline telephone service. FIG. 15C depicts mobile computer device 906 with button 1005 communicating with static computer device 906, which in turn activates telephone device 1010 to send one or more messages to one or more recipients over the landline telephone service, thus allowing a remote user to perform one or more activities over a physical system (i.e., a landline telephone system, a cable internet system, etc.).

FIGS. 16A-16K illustrate one implementation of a menu system and other screenshots for system software 401 that typically may be installed on each computer device 906 in system 100. The illustrations in FIGS. 16A-16k underscore certain of the functionalities of system 100 and the "look and feel" of the system software 401. It is to be noted that the illustrated menu system and screenshots are exemplary only. Other menu systems and screenshots may be readily developed and provide additional functionalities and capabilities.

Figure 16A:
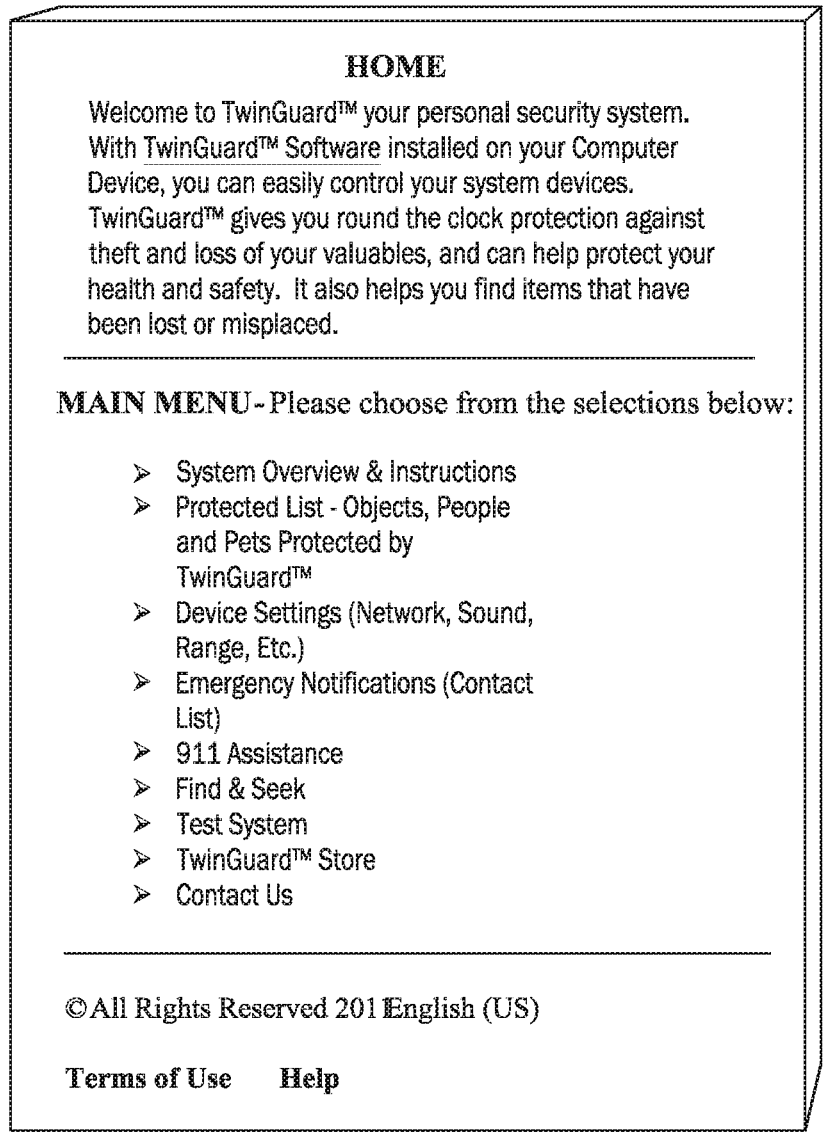
FIG. 16A illustrates screenshot of the System of FIG. 9, more specifically a Home page.

FIG. 16A depicts Main menu 801, which typically may be a sample screenshot of a Home Page and main menu 801 of system software program 401 for computer devices 906 in system 100. Main Menu 801 gives users various options for configuring and/or using system; obtaining answers to questions; configuring system devices; checking the status of system devices; purchasing additional devices; setting up 911 messages and/or alerts; etc. The selections of subpages accessed through main menu 801 typically are illustrated in 802-810 on FIGS. 16B-16K, respectively. By clicking on a link to a subpage in main menu 801, the user may be taken to the relevant subpage. From any subpage 802-810, by clicking on a main menu link, the user typically may be returned to home/main menu 801.

FIG. 16B depicts System Overview and Instructions page 802, which typically provides the user with brief descriptions of different system components and/or software features. This page typically instructs the user in the operation of the system/program and/or describes its component devices and/or functions. By clicking on any definitional and/or descriptive item highlighted on this page, the user may either be taken to another subpage with information and/or actions the user may perform (e.g., programming and/or testing devices), and/or the user may be taken to another subpage providing further information and/or definitions.

FIG. 16C depicts Protected List page 803, which typically provides the user with a detailed inventory of devices 102 in system 100; objects, people, and/or pets 903 with which sensor devices 102 may be associated; and/or the range, sound and/or volume settings for each system device. The page also allows the user to see the status ("on" and/or "off") of system devices, and/or to see settings for any controller device 101 with a panic button 1005 functionality (e.g., the number of clicks needed to summon police assistance; whether silent dialing is turned on and/or off; and/or whether audible alarm sounds may be activated). Finally, from this page, the user may see the types of alert messages and/or recipients that have been programmed into system 100. The user may modify settings shown on this page and/or add information by clicking on a "Device Settings" link; and/or may also modify and/or add contacts and/or messages for alerts by clicking on an Emergency Notification link (i.e., the parties that may be notified automatically by delivery from computer device 906 of a preset message).

Figure 16D:
FIG. 16D illustrates screenshot of the System of FIG. 9, more specifically a Device Settings page.
Figure 16H:
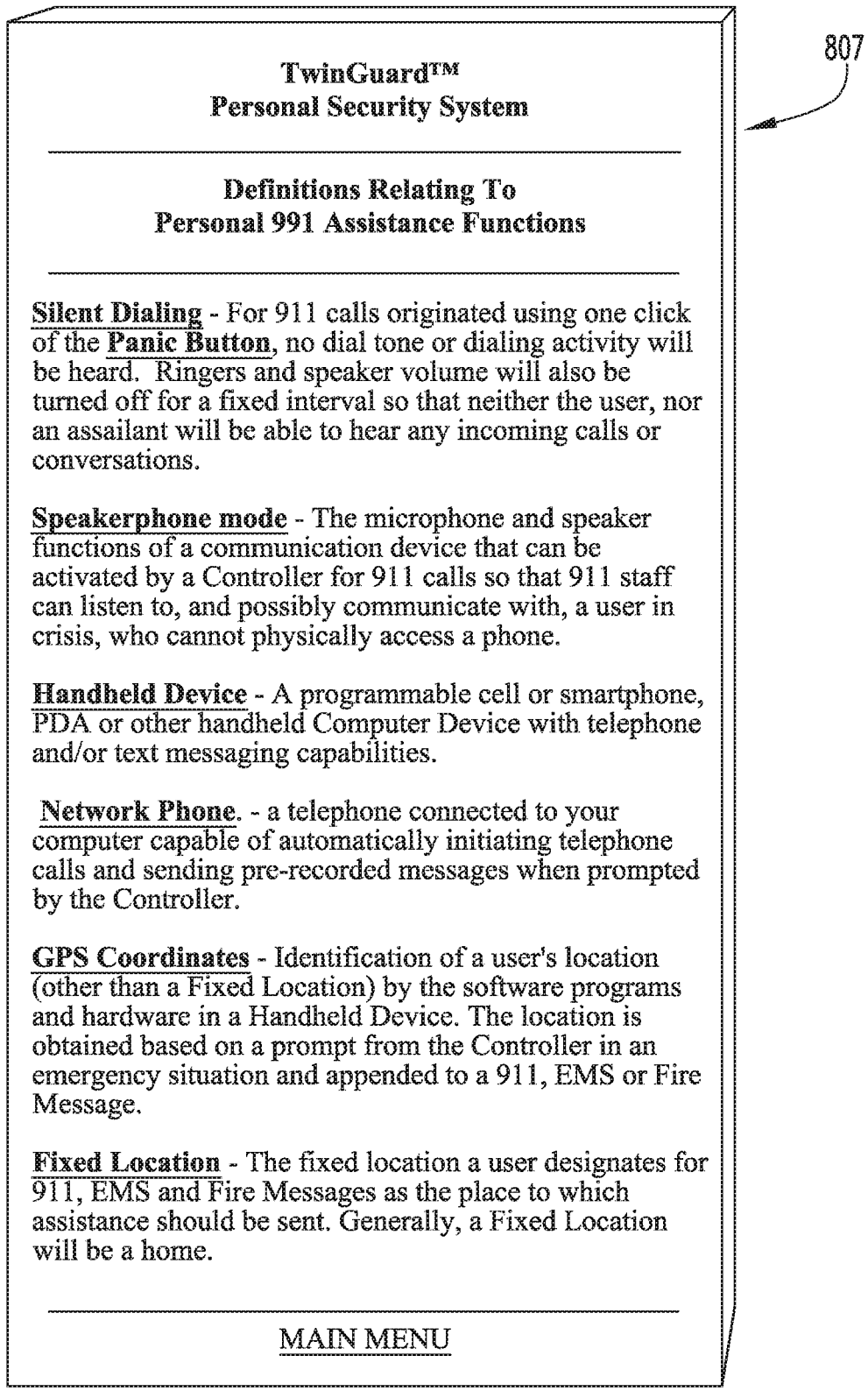
FIG. 16H illustrates screenshot of the System of FIG. 9, more specifically a second Definitions page.

FIG. 16D depicts Device setting page 804, which typically contains programming instructions and allows users to input information to program system devices. From this page, the user may be able to click on links to subpages where specific actions may be taken. Those actions include (i) programming alarm sounds and/or distances/ranges for sensors 102 and/or controller 101 (if included in system 100); turning devices on and off; associating sensors 102 with objects, people, and/or pets 903; and/or setting up emergency notifications in the event of certain losses and/or other situations.

FIG. 16E depicts Emergency notifications page 805, which typically lets a user configure notices that may be sent to the user and/or other third parties. Those notices may be sent in certain cases where the computer device 906 detects the loss of an object, person, and/or pet wearing, carrying and/or to which there is affixed, a sensor 102. Through various drop-down menus, the user may be able to specify recipients of notifications; enter contact information for the user and/or designated recipients; elect to use and/or customize predefined messages; specify which sensor devices 102 typically may trigger alert notices in the event they are taken and/or lost; etc. Notification messages typically may be delivered to recipients by voice and/or text and/or email messages, subject to the hardware and/or software capabilities of the user's computing device 906 and/or 701. For example, the system software 401 may include voice-to-text messaging (i.e., typically may cause the computer device 906 to type messages based on the user's spoken words); and/or typically may provide for text-to-voice messaging (i.e., typically may cause the computer device 906 to verbally play back for 911 and/or other third parties messages that have been prewritten for the program and/or that are recorded by the user).

FIG. 16F depicts 911 assistance page 806, which typically contains instructions for using, and governs the operation of, the automated emergency dialing features of system 100 where controller device 101 may be equipped with a panic button 1005. This page allows users to control various settings and/or features related to automated dialing services. As discussed elsewhere in this application, based on the number of times a user clicks (presses) on actuator/panic button 1005, automated calls typically may be made through computer device 906 to 911 requesting police, EMS, and/or fire rescue services. Operationally, the computer device 906 may typically be in range of the controller 101 when panic button 1005 is pressed. Once computer device 906 receives the signal through wireless communication link 201, system software 401 causes computer device 906 to, typically immediately, dial 911 and/or play a prerecorded message requesting assistance for the user and/or explaining that the user cannot physically access the phone. Through this screen page 806, the user may set various parameters for the 911 dialing features, including (i) activating "silent dialing" and/or speaker silencing so that an assailant is not alerted to the call; (ii) including personalized information (e.g., medical conditions, allergies, etc.) in messages to 911; sending copies of 911 messages to third parties specified by the user (based on their contact information stored in computer device's 906 memory 110); adding automated GPS positioning messages to 911 messages; and/or selecting the type of messages to be sent to third parties (i.e., voice, text, email, and/or the like). To further facilitate the understanding and/or use of automated 911 dialing and/or panic button 1005 functionality, through the drop down menu on 911 assistance page 806, a user accesses separate subpages with definitions and explanations 807, depicted on FIGS. 16G-16H.

Figure 16I:
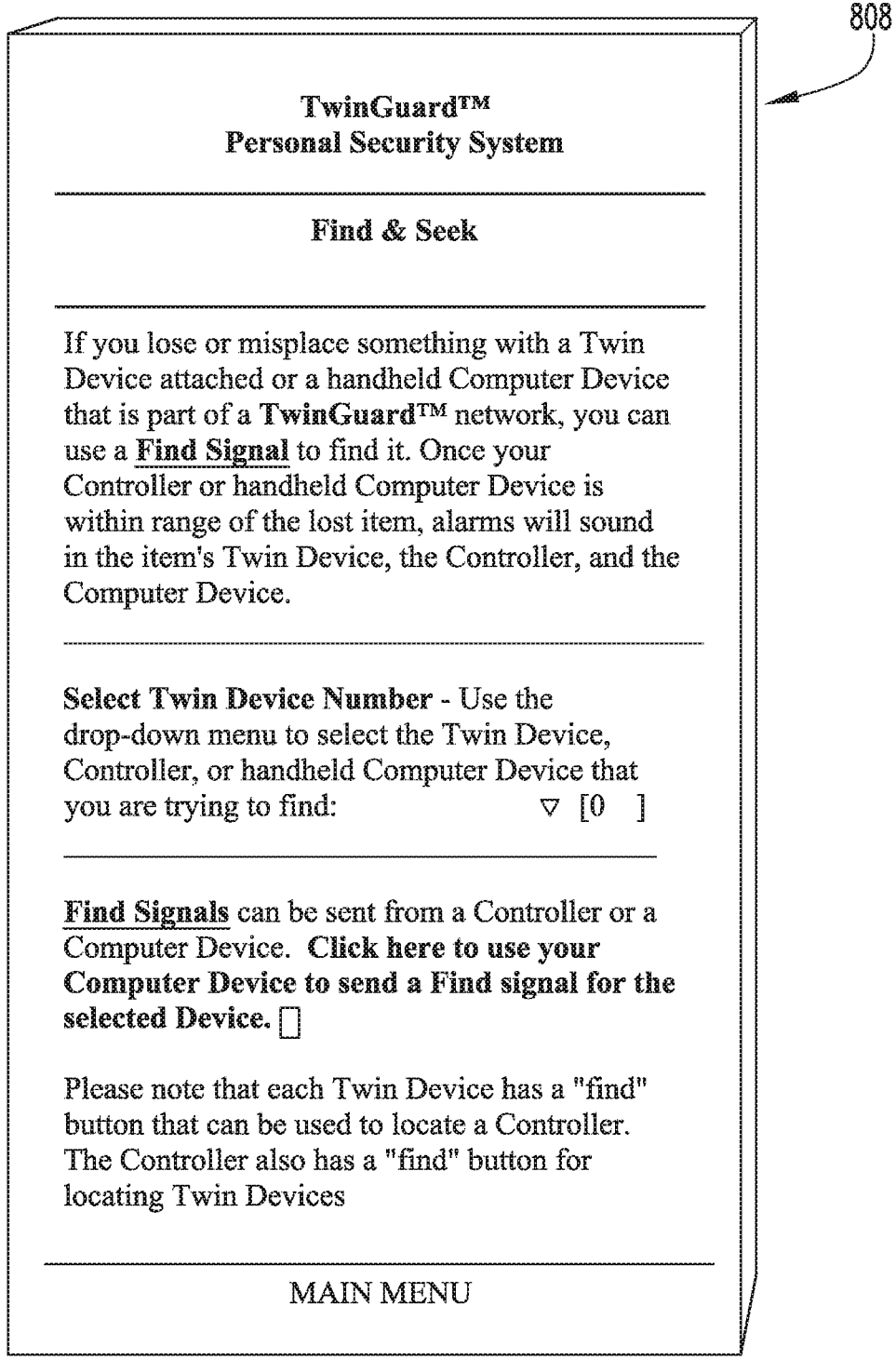
FIG. 16I illustrates screenshot of the System of FIG. 9, more specifically a Find and Seek page.

FIG. 16I depicts use of functions and/or directions on Find and Seek page 808, which typically allows users to cause computing device 906 to find objects, people, and/or pets that have been lost. From a dropdown menu, the user may select a sensor 102 that may be attached to an item that has been lost (e.g., an eyeglass case with a sensor 102 affixed to it that has been misplaced in the home). By clicking on the relevant device name and/or number on this subpage, the user may cause computer device 906 to send a signal to lost sensor 102. If lost sensor 102 is within computer device's 906 maximum range (determined by wireless communication system 201), sensor 102's distinct alarm sound typically may be activated in sensor 102 and/or computer device 906 for a preset period of time (e.g., one, five, ten, twenty, etc. minutes).

Figure 16J:
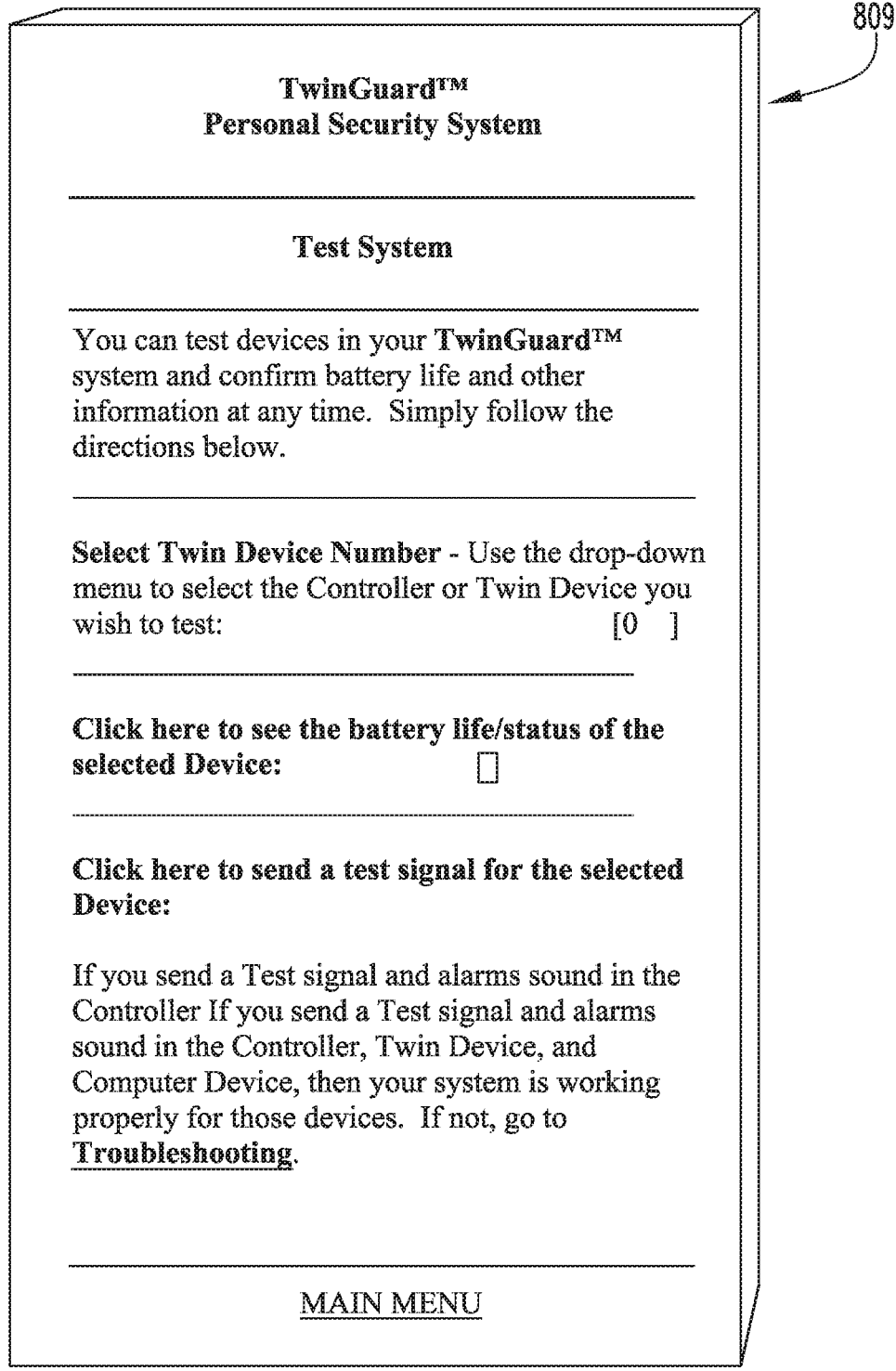
FIG. 16J illustrates screenshot of the System of FIG. 9, more specifically a Test System page.

FIG. 16J depicts Test System screen page 809, which typically allows a user to test the operating status of devices in system 100 to make sure they may be operational, charged (in relation to battery life), etc. Using a dropdown menu, the user may select each system device (i.e., controller 101 and/or sensors 102) to be tested. By following the instructions and/or clicking on the specified device, alarm sounds typically may be triggered if it is working. If not working, the user may seek solutions by clicking on a link to a Troubleshooting subpage.

Figure 16K:
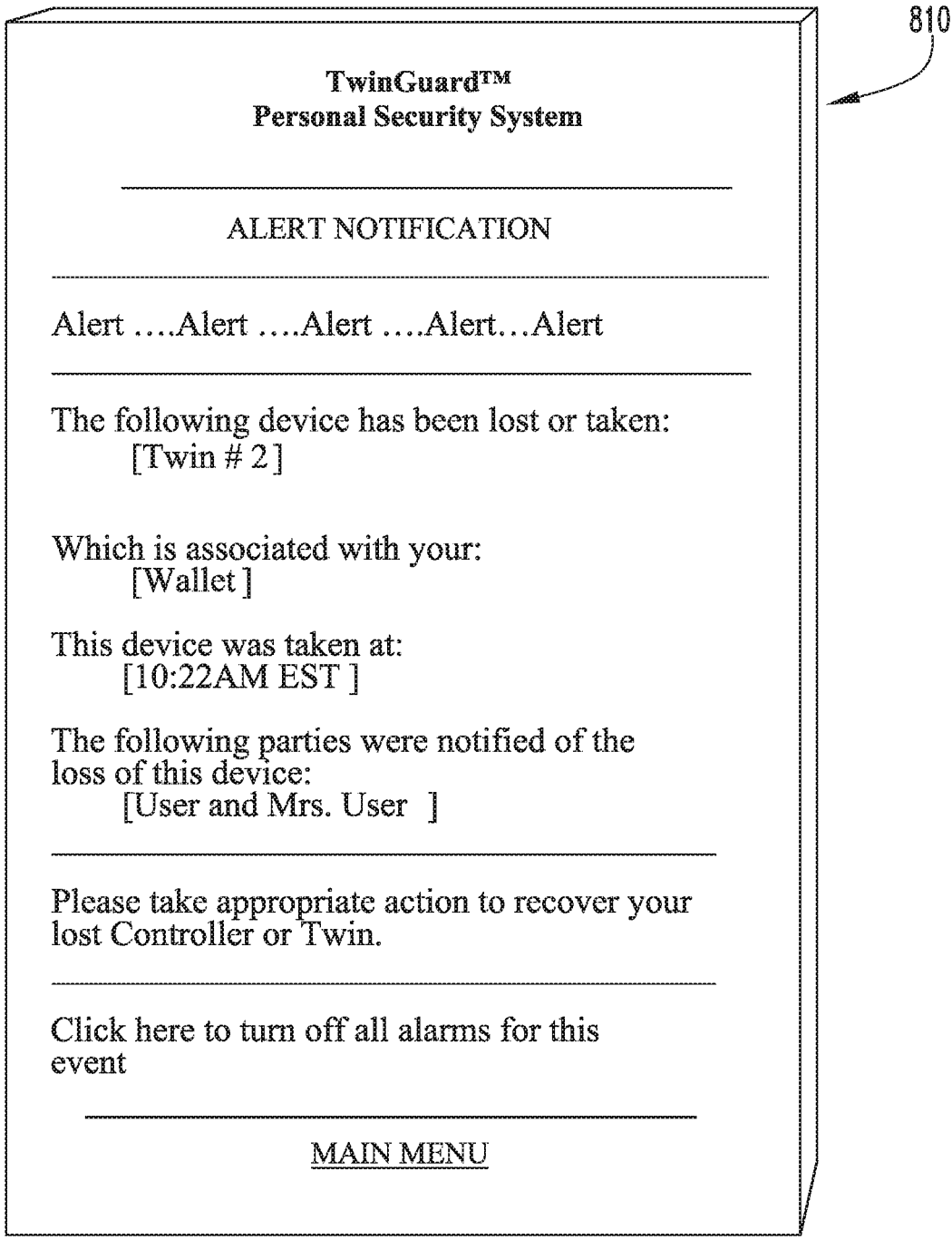
FIG. 16K illustrates screenshot of the System of FIG. 9, more specifically an Alerts page.

FIG. 16K depicts Alert Notification screen page 810, which typically provides a user with a visual display notifying that a breach has occurred in system 100. This screen flashes on and off at the same time that vibration and/or sound alarms are playing in the computer device 906. The screen also provides pertinent information to the user as to the nature of the breach, which may include (i) the identification of the controller 101 and/or sensor 102 that has been taken (i.e., moved out of the predetermined range and/or distance) from the controller 101 and/or computer device 906; (ii) the object, person, and/or pet associated with the device (if it is a sensor 102); the time of the breach; and (iv) the parties notified of the breach. The screen may also let the user turn off all alarms.

Figure 17A:
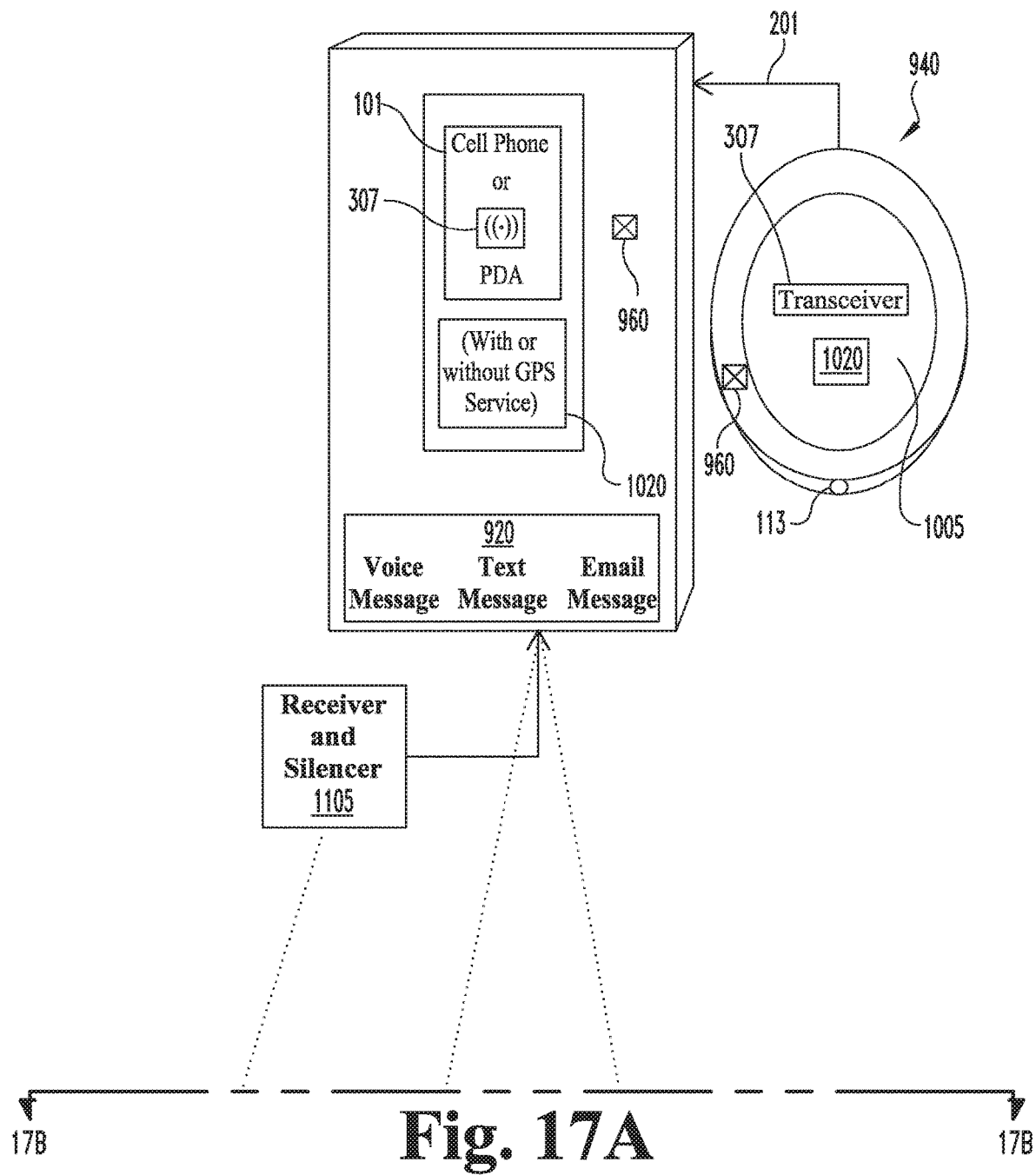
FIG. 17A depicts a first block diagram associated with the System of FIG. 9, including a communication device enabled for remote activation of emergency call functionality in the FIG. 9.
Figure 17B:
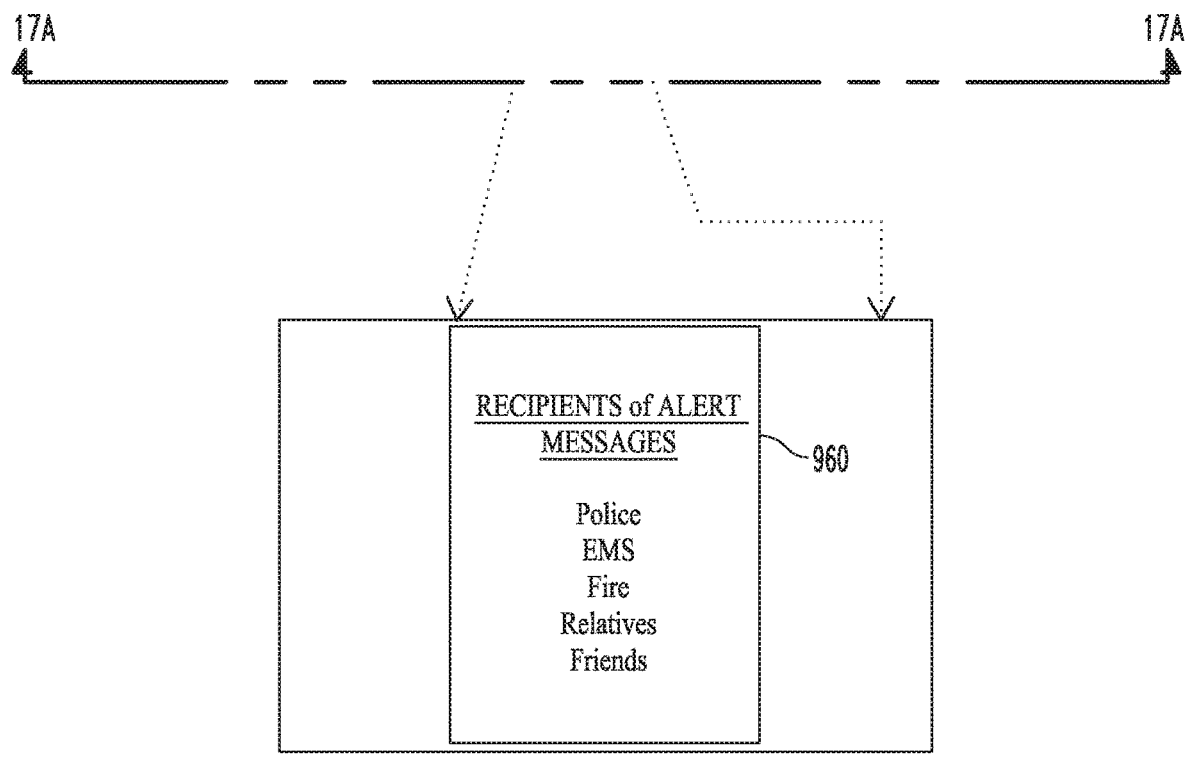
FIG. 17B depicts a second block diagram associated with the System of FIG. 9, including a communication device enabled for remote activation of emergency call functionality in the FIG. 9.

As illustrated in FIGS. 17A-17B, another implementation of the present novel technology relates automatically initiating a remote emergency call from a cellular telephone, PDA, portable computer and/or like communication device that may function like controller 101. System 100 typically includes cellular telephone and/or other communication device (such as a PDA) 101 that has been preprogrammed with an emergency voice, text, and/or email message and/or messages 920 and which likewise includes a BLUETOOTH, infrared, and/or like communication system 307 for receiving a call and/or message initiation signal. Typically, cellular telephone and/or PDA device 101 also includes a GPS location device 1020 for assessing its location and/or providing the same as part of and/or in addition to message(s) 920.

The system 100 further includes a remote actuator device 940 for signaling controller device 101 to initiate the call, text, and/or email message(s). Typically, remote actuator device 940 includes a transceiver 307 for communicating an activation signal over communication link 201 to controller 101 and/or an actuator switch 1005 for actuating the same. Transceiver 307 may be typically connected to power source 113, such as a battery, for generating the signal.

In operation, remote actuator device 940, having the form of a fob and/or like object, may be actuated by its trigger switch and/or button 1005 in an emergency situation. Transceiver 307 emits actuation signal, which may be received by cellular telephone and/or PDA device 101, initiating telephone and/or PDA device 101 to transmit its emergency message 920. Typically, message 920 may be a 911 call and/or the like (which may include a voice message and/or a text and/or email message), but may also be individualized in content and/or destination (e.g., a message may be sent to EMS and/or the police based on local 911 services; but may also be sent to a spouse, parent, and/or the like). Message 920 may typically include GPS location information. The message may also be different based on different "clicks" of the transceiver. For example, one click may be programmed to send a message such as "Help: I'm being assaulted; cannot speak; and/or need assistance immediately at the following address;" two clicks may be programmed to send a message such as "I'm in a medical crisis; cannot speak on the phone; and/or need emergency medical services immediately at the following address;" and/or three clicks may be programmed to send a message such as "there is a fire; send fire rescue." Initiation of message 920 may likewise cue controller 101 for remote querying of its location by responders and/or remote audio and/or video monitoring of the situation. Remote device 910 may be either physically activated by clicking and/or pressing a trigger switch and/or button 1005 and/or may be voice activated. For a voice activation model, the device 940 may include a microphone capable of detecting voice commands and/or sending a signal to the phone and/or PDA device 101 activating a call and/or delivery of a text and/or email message to the police, EMS, and/or other recipients 960.

For alerts involving threat to life and/or limb, system 100 may need to be silently activated and/or silenced, for example using receiver/silencer device 1105 so as not to alert and/or antagonize an assailant. Receiver/silencer 1105 may receive a signal from transceiver 307 and initiate one or more commands to cell phone/PDA device 101 including, but not limited to, turning on/off the phone/PDA device 101; transmitting voice and/or data (e.g., text messages, emails, and/or the like); initiating silent modes for system 100 (e.g., in event of an imminent assault, dialing out and/or sending messages silently so assailant cannot hear call for help, shutting off speaker 112 so that assailant cannot hear responses from emergency services or others, activating and/or sending GPS coordinates, and/or the like), and/or the like. System 100 may also shut off voice response from a call recipient 960. In other words, once an emergency message 920 is sent to the police, the controller 101 may need to cut off incoming conversation so as to avoid an assailant overhearing a conversation from the responder. In other implementations, the override system may not be needed for a summons to EMS not involving physical assault.

While the novel technology has been illustrated and described in detail in the drawings and foregoing description, the same is to be considered as illustrative and not restrictive in character. It is understood that the embodiments have been shown and described in the foregoing specifications in satisfaction of the best mode and enablement requirements. It is further understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

While a particular embodiment of the present invention has been shown and described, modifications may be made. It is therefore intended in the appended claims to cover such changes and modifications which follow in the true spirit and scope of the invention.

What is claimed is:

1. A personal security system for automatically alerting a user due to an excessive distance threshold condition, comprising:
    a plurality of transceivers;
    a controller device having a communication link with each of the plurality of transceivers, wherein the controller device is programmed to distinguish each transceiver by its unique digital signature, wherein the communication link between the controller device and each transceiver has a predetermined operating distance;
    at least one of a stationary computer device or a handheld computer device having a communication link with the controller device to program the controller device to control settings for each transceiver;
    wherein, when the controller device and any one of the transceivers are separated by a separation distance exceeding the predetermined operating distance for a predetermined duration, the controller device and the transceiver separated from the controller device by the predetermined operating distance generate a unique predetermined alarm indicator;
    wherein, after being so separated, when the controller device and the transceiver separated from the controller device are brought back within the predetermined operating distance, the controller device and the transceiver separated from the controller device generate the unique predetermined alarm indicator.

2. The personal security system of claim 1, wherein the controller device is programmed to communicate a separate digital signal recognized by each transceiver through a wireless communication system.

3. The personal security system of claim 1, further comprising:
    the stationary computer device or the hand-held computer device are capable of functions selected from the group consisting of telephonic, messaging, email, and combinations thereof;
    a graphical user interface including a display screen operationally connected to the stationary computer device or the hand-held computer device;
    a vibration device operationally connected to the stationary computer device and the hand-held computer device;
    a sound device operationally connected to the stationary computer device and the hand-held computer device;
    wherein the stationary computer device or the hand-held computer device is configured to recognize digital signals, make preset responses to digital signals, and respond to digital signals to program optional settings and respond in a preset way;
    wherein the stationary computer device or the hand-held computer is capable of displaying information in response to digital signals;

wherein the memory of the stationary computer device or the hand-held computer device is capable of storing a database containing contact information;

wherein the memory of the stationary computer device or the hand-held computer device is capable of storing optional settings;

wherein the memory of the stationary computer device or the hand-held computer device is capable of storing messages; and wherein the stationary computer device or the hand-held computer device is configured to automatically send at least one message to at least one recipient in response to digital signals from the transceivers.

4. The personal security system of claim 3, wherein the at least one message is selected from the group comprising voice messages, text messages, and email messages.

5. The personal security system of claim 3, wherein upon separation of at least one of the transceivers and the stationary computer device or the hand-held computer device by a distance exceeding the predetermined operating distance, the stationary computer device or the held-held computer device generates the unique predetermined alarm indicator, and the at least one of the transceivers generates the unique predetermined alarm indicator;

wherein, after being so separated, the at least one of the transceivers and the stationary computer device or hand-held computer device are brought back within the predetermined operating distance, the stationary computer device or the hand-held computer device again generates the unique predetermined alarm indicator and the at least one of the transceivers again generates the unique predetermined alarm indicator; and wherein the stationary computer or the hand-held computer is capable of automatically delivering the at least one message upon separation from the at least one of the transceivers.

6. The personal security system of claim 1, wherein the unique predetermined alarm indicator corresponding to each of the transceivers is a unique alarm sound.

7. The personal security system of claim 6, wherein, if more than one of the transceivers is separated from the controller device by a separation distance exceeding the predetermined operating condition, the controller device intermittently plays the unique alarm sound for each of the more than one transceivers.

* * * * *